(12) United States Patent
Fahl et al.

(10) Patent No.: US 7,414,154 B2
(45) Date of Patent: Aug. 19, 2008

(54) POLYAMINE COMPOUNDS AND COMPOSITIONS FOR USE IN CONJUNCTION WITH CANCER THERAPY

(75) Inventors: William E. Fahl, Madison, WI (US); Richard R. Copp, Jr., Oregon, WI (US); Cynthia E. Ochsner, Madison, WI (US); Daniel D. Peebles, Fond du Lac, WI (US); Kathleen L. Fahl, Madison, WI (US)

(73) Assignee: Wisconsin Alumni Research Foundation, Madsion, WI (US)

( * ) Notice: Subject to any disclaimer, the term of this patent is extended or adjusted under 35 U.S.C. 154(b) by 322 days.

(21) Appl. No.: 10/847,236

(22) Filed: May 17, 2004

(65) Prior Publication Data

US 2004/0225021 A1 Nov. 11, 2004

Related U.S. Application Data

(63) Continuation of application No. 10/360,195, filed on Feb. 7, 2003, now abandoned.

(60) Provisional application No. 60/355,356, filed on Feb. 7, 2002.

(51) Int. Cl.
*C07C 215/24* (2006.01)
*C07C 211/22* (2006.01)
*A61K 31/131* (2006.01)

(52) U.S. Cl. ............... 564/509; 564/503; 564/507; 564/512; 514/665; 514/671; 514/674

(58) Field of Classification Search ............... None
See application file for complete search history.

(56) References Cited

U.S. PATENT DOCUMENTS

| | | | |
|---|---|---|---|
| 3,773,833 A | 11/1973 | Henrici et al. | 564/509 |
| 5,217,964 A | 6/1993 | Edwards et al. | 514/104 |
| 5,292,497 A | 3/1994 | Schein et al. | 424/10 |
| 5,434,145 A | 7/1995 | Edwards et al. | 514/108 |
| 5,541,230 A | 7/1996 | Basu et al. | 514/642 |
| 5,627,215 A | 5/1997 | Frei et al. | 514/674 |
| 5,889,061 A | 3/1999 | Frydman et al. | 514/674 |
| 5,962,533 A | 10/1999 | Bergeron, Jr. | 514/674 |
| 6,172,261 B1 | 1/2001 | Vermeulin et al. | 564/84 |
| 6,239,119 B1 | 5/2001 | Stogniew et al. | 514/131 |
| 2003/0022867 A1 | 1/2003 | Stogniew et al. | 514/114 |
| 2003/0118539 A1 | 6/2003 | Fahl et al. | 424/70.17 |

FOREIGN PATENT DOCUMENTS

| | | |
|---|---|---|
| WO | WO 94/19311 | 9/1994 |
| WO | WO 94/27961 | 12/1994 |
| WO | WO 98/17624 | 4/1998 |
| WO | WO 00/66587 A2 | 11/2000 |
| WO | WO 00/78289 | 12/2000 |
| WO | WO 01/85142 A1 | 11/2001 |
| WO | WO 02/38105 A2 | 5/2002 |
| WO | WO 03/013245 A1 | 2/2003 |

OTHER PUBLICATIONS

Database CAPLUS on STN, Acc No. 1999:77533, Vermeulin et al., WO 9903823 (Dec. 8, 1999) (CAPLUS abstract).*
Database CAPLUS on STN, Acc. No. 1971:437363, Yamauchi et al., JP 45034456 (Nov. 5, 1970) (abstract).*
Supportive Care in Cancer, 2004, 12(8), p. 543-549.*
Supportive Care in Cancer, 1997, 5(2), p. 139-143 (abstract).*
Cancer Treatment Reviews, 2006, 32(8), p. 645-651.*
The PCT International Search Report dated Jul. 11, 2003 (PCT/US03/03607).
Aprahamian, M., et al., "Transmucosal passage of polyalkylcyanoacrylate nanocapsules as a new drug carrier in the small intestine," *Biol. of the Cell*, 1987, 61, 69-76.
Basu, H.S., et al., "The interaction of spermine and pentamines with DNA," *Biochem. J.*, 1987, 244, 243-246.
Basu, H.S., et al., "Effects of variation in the structure of spermine on the association with DNA and the aduction of DNA conformational changes," *Biochem. J.*, 1990, 269, 329-334.
Chen, G., et al., "Protection against cyclophosphamide-induced alopecia and inhibition of mammary tumor growth by topical 1,25-dihydroxyvitamin $d_3$ in mice," *Int. J. Cancer*, 1998, 75, 303-309.
Creaven, P.J., et al., "Unusual central nervous system toxicity in a phase I study of $N^1N^{11}$ diethylnorspermine in patients with advanced malignancy," *Invest. New Drugs*, 1997, 15, 227-234.
Ellouk-Achard, S., et al., "Ex Vivo and in Vitro models in acetaminophen hepatotoxicity studies. Relationship between glutathione depletion, oxidative stress and disturbances in calcium homeostasis and energy metabolism," *Arch. Toxicol. Suppl.*, 1995, 17, 209-214.
Feuerstein, B.G., et al., "Molecular dynamics of spermine-DNA interactions: sequence specificity and DNA bending for a simple ligand," *Nuc. Acids Res.*, 1989, 17(17), 6883-6892.
Ho, D., et al., "Modification of glutathione levels in C3H/10T1/2 cells and its relationship to benzo(α)pyrene anti-7,8-dihydrodiol 9,10-epoxide-induced cytotoxicity," *J. Biol. Chem.*, Sep. 24, 1984, 259(18), 11231-11235.
Huber, M., "2,2' -Dithiobis(N-ethyl-spermine-5-carboxamide) is a high affinity, membrane-impermeant antagonist of the mammalian polyamine," *J. of Biol. Chem.*, 1996, 271(44), 27556-27563.
Hussein, A.M., et al., "Protection from chemotherapy-induced alopecia in a rat model," *Science*, Sep. 28, 1990, 249, 1564-1566.
Kramer, D.L., et al., "Polyamine analogue induction of the p53-$p21^{WAF1/CIP1}$-Rb pathway and $G_1$ arrest in human melanoma cells," *Cancer Res.*, Mar. 15, 1999, 59, 1278-1286.
Kramer, D.L., et al., "Effects of novel spermine analogues on cell cycle progression and apoptosis in MALME-3M human melanoma cells," *Cancer Res.*, Dec. 15, 1997, 57, 5521-5527.

(Continued)

*Primary Examiner*—Brian J Davis
(74) *Attorney, Agent, or Firm*—Quarles & Brady LLP

(57) ABSTRACT

The invention provides novel polyamine compounds and pharmaceutical compositions for administration in conjunction with cancer chemotherapy or radiation therapy. The compounds are administered locally to provide protection against the adverse side-effects of chemotherapy or radiation therapy, such as alopecia, mucositis and dermatitis. Pharmaceutical preparations comprising one or more chemoprotective polyamines formulated for topical or local delivery to epithelial or mucosal cells are disclosed. Methods of administering the pharmaceutical preparations are also disclosed.

42 Claims, 12 Drawing Sheets

OTHER PUBLICATIONS

Levy, E.J., et al., "Transport of glutathione diethyl ester into human cells," *Proc. Natl. Acad. Sci. USA*, Oct. 1, 1993, 90(19), 9171-9175.

March, J., Advanced Organic Chemistry: Reactions, Mechanisms, and Structure, 4th Ed., *John Wiley & Sons*, New York, 1992, 771-780.

Masuda, K., et al., "Response of previously irradiated mouse skin to a second course of irradiation: early skin reaction and skin shrinkage," *Int. J. Radiation Oncol. Biol. Phys.*, 1986, 12, 1645-1651.

Sonis, S.T., et al., "Defining mechanisms of action of interleukin-11 on the progression of radiation-induced oral mucositis in hamsters," *Oral Oncology*, 2000, 36, 373-381.

Spotheim-Maurizot, M., "Radioprotection of DNA by polyamines," *Int. J. Radiat. Biol.*, 1995, 68(5), 571-577.

Streiff, R., et al., "Phase 1 study of $N^1$-$N^{11}$-diethylnorspermine (DENSPM) administered TID for 6 days in patients with advanced malignancies," *Invest. New Drugs*, 2001, 19, 29-39.

U.S. Appl. No. 09/565,714, filed May 5, 2000, Fahl et al.

U.S. Appl. No. 10/214,917, filed Aug. 7, 2002, Fahl et al.

Alvarez, E., et al., "Preclinical characterization of CG53135 (FGF-20) in radiation and concomitant chemotherapy/radiation-induced oral mucositis," *Clin. Cancer Research*, 2003, 9, 3454-3461.

Basu, H., et al., "Correlation between the effects of polyamine analogues on DNA conformation and cell growth," *Cancer Res.*, 1989, 49, 5591-5597.

Desai, M.P., et al., "The mechanism of uptake of biodegradable microparticles in Caco-2 cells is size dependent," *Pharm. Res.*, 1997, 14(11), 1568-1573.

Gao, X., et al., "Radioprotective effect of epinephrine as a vasoconstrictor in mouse oral mucosa and scalp," *Okayama Igakkai Zasshi*, 1996, 108, 139-144 (Translation).

Hillery, A.M., et al., "Comparative, quantitative study of lymphoid and non-lymphoid uptake of 60nm polystyrene particles," *J. Drug Targeting*, 1994, 2, 151-156.

Jayaraman, S.C., et al., "Topical delivery of erythromycin from various formulations: an in vivo hairless mouse study," *J. Pharm. Sci.*, 1996, 85, 1082-1084.

Jeitner, T.M., et al., "Inhibition of the proliferation of human neural neoplastic cell lines by cysteamine," *Cancer Lett.*, 1996, 103, 85-90.

Kramer, D.L., et al., "Polyamine depletion in human melanoma cells leads to $G_1$ arrest associated with induction of $p21^{WAF1/CIP1/SDI1}$, changes in the expression of p21-regulated genes, and a senescence-like phenotype," *Cancer Res.*, 2001, 61, 7754-7762.

Lowy, R.O., et al., "Protection against local irradiation injury to the skin by locally and systemically applied drugs," *Radiation Biology*, 1972, 105, 425-428.

Purdie, J.W., "A comparative study of the radioprotection effects of cysteamine, WR-2721, and WR-1065 in cultured human cells," *Radiation Res.*, 1979, 77, 303-311.

Snyder, R.D., et al., "Further evidence that the radioprotective aminothiol, WR-1065, catalytically inactivates mammalian topoisomerase II," *Cancer Res.*, 2000, 60, 1186-1188.

Verhey, L.J., et al., "Determination of the radioprotective effects of topical applications of MEA, WR-2721, N-acetylcysteine on murine skin," *Radiation Res.*, 1983, 93, 175-183.

\* cited by examiner

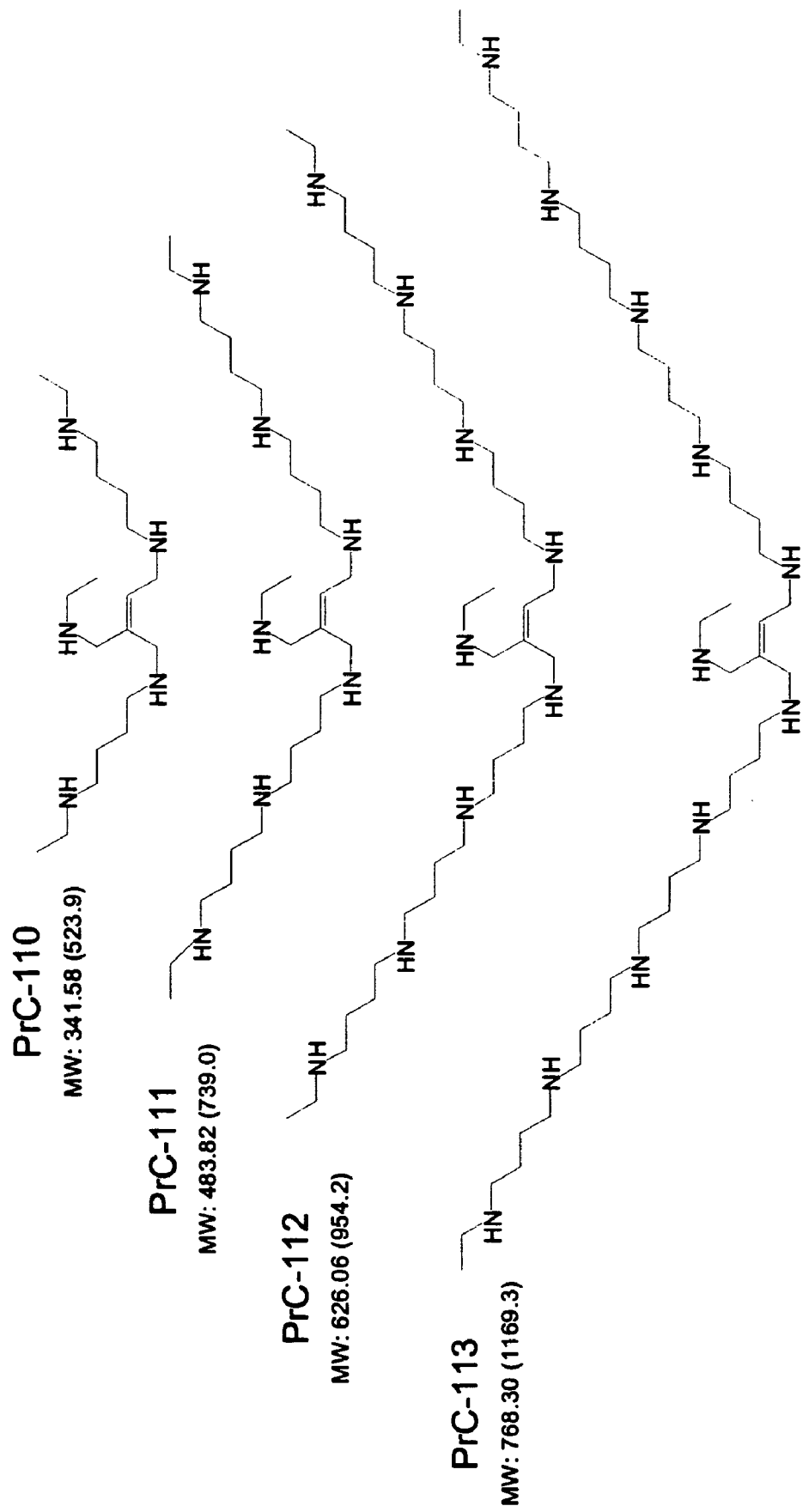

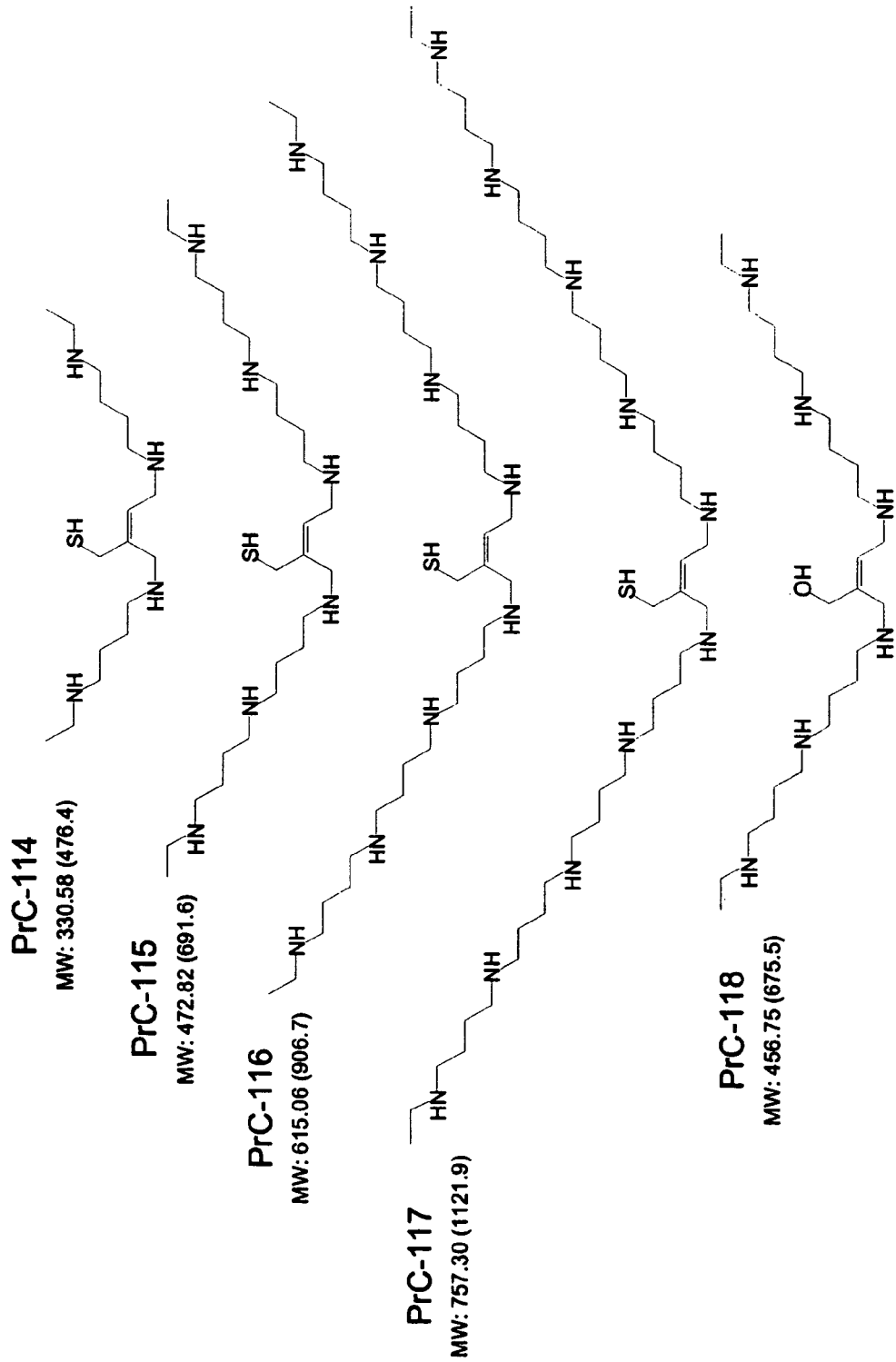

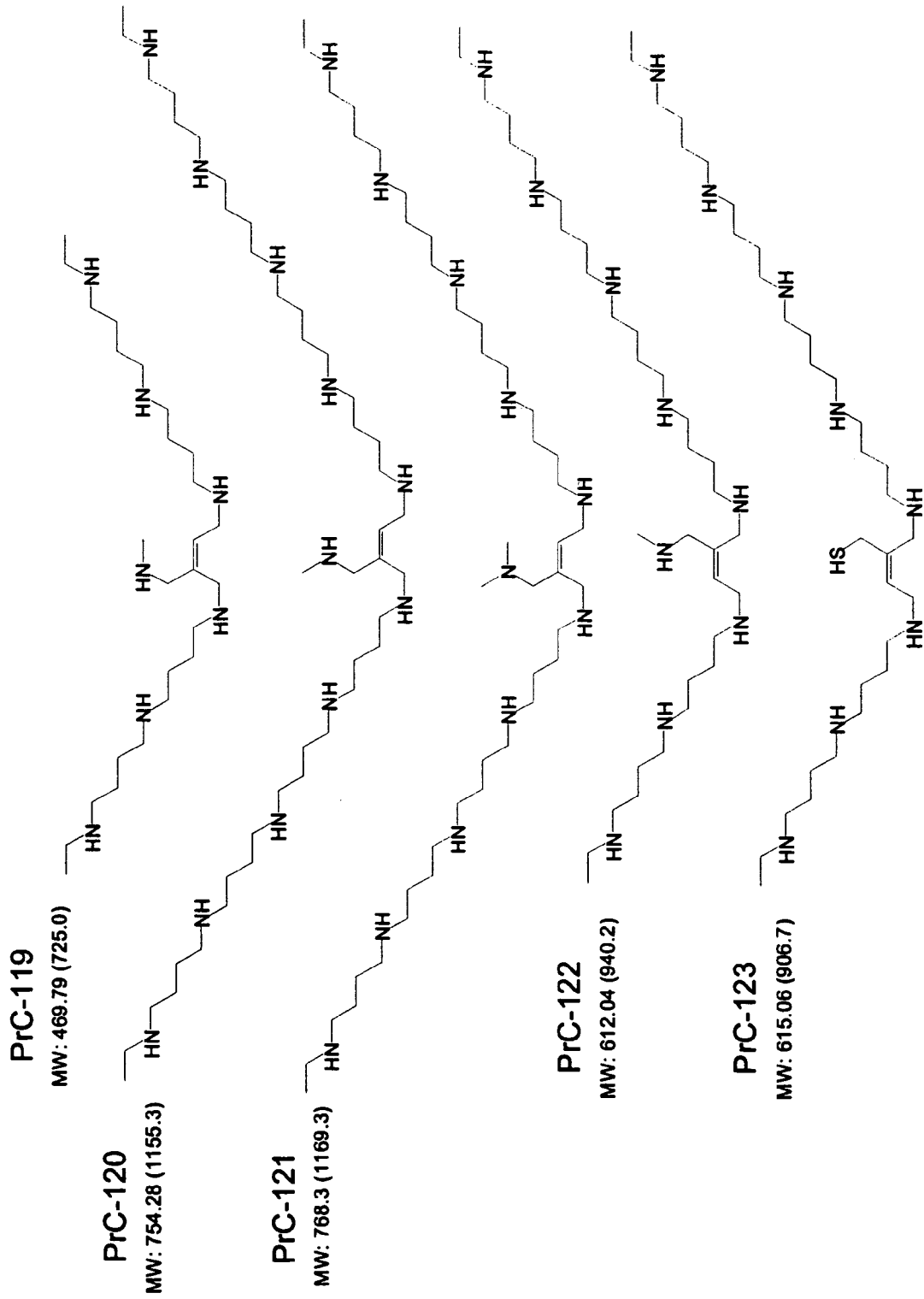

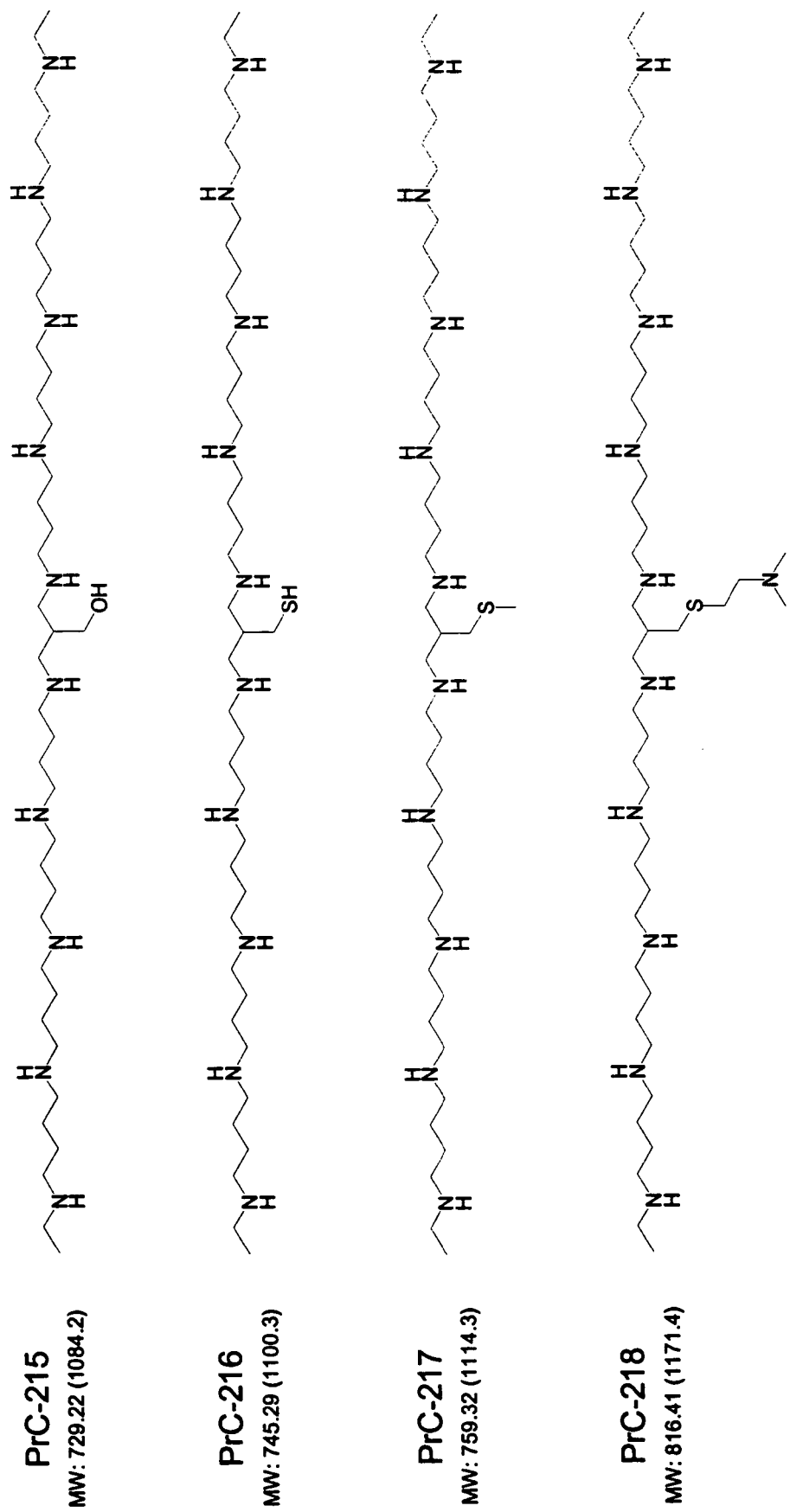

Human Dermal Fibroblasts

Human Dermal Fibroblasts

POLYAMINE COMPOUNDS AND COMPOSITIONS FOR USE IN CONJUNCTION WITH CANCER THERAPY This application is a continuation of U.S. application Ser. No. 10/360,195, filed Feb. 7, 2003 now abandoned which claims benefit of U.S. Provisional Application No. 60/355,356, filed Feb. 7, 2002, the entirety of each of these applications is incorporated by reference herein.

Pursuant to 35 U.S.C. §202 (c), it is acknowledged that the United States Government has certain rights in the invention described herein, which was made in part with funds from the National Institutes of Health, Grant No. CA22484.

FIELD OF THE INVENTION

The present invention relates to the field of cancer therapy. In particular, the invention provides novel polyamine compounds and pharmaceutical compositions for reducing or preventing toxic side effects of radiotherapy and cancer chemotherapeutic agents.

BACKGROUND OF THE INVENTION

Various patents and other publications are referenced in this application in order to more fully describe the state of the art to which this invention pertains. The disclosure of each of these publications is incorporated by reference herein, in its entirety.

It is well known that the use of chemotherapy and radiotherapy to treat cancer patients is associated with severe side effects due to the toxicity of such treatments to epithelial cell populations, including stem cells within the hair follicle, skin epidermis and gastrointestinal mucosa.

Currently, there are no treatments to prevent cancer therapy side effects. Effective treatments would likely include molecules that i) inhibit or slow growth of the at-risk cells, ii) modify the cellular DNA of the at-risk cells to make it less easily damaged, and iii) provide some means with which to scavenge electrophilic drug metabolites or oxygen radicals formed during irradiation.

Polyamines have been proposed as growth regulators. DENSPM, a synthetic analog of spermine, has been shown to decrease cell growth (Kramer et al., Cancer Res. 57:5521-5527, 1997), and has been studied in an early stage clinical trial as an antineoplastic drug (Creaven, P. et al., Invest. New Drugs 15:227-234, 1997; Streiff, R and Bender, J., Invest. New Drugs 19:29-39, 2001). The clinical trials, however, were aborted because of the serious side effects in multiple organ sites that were associated with the systemic use of this polyamine analog. These results teach that molecules used to decrease division of healthy stem cells that are at risk from cancer therapy would need to create a transient cell cycle block and would need to be applied topically to achieve local delivery to epithelial cells, with little or no systemic delivery, or if any, low enough to preclude protection of systemic cancer cells or induction of systemic side effects.

Naturally occurring polyamines, such as spermine, have been shown to bind to nucleic acids and to induce structural changes in helical DNA (Basu, H. and Marton, L., Biochem. J. 244:243-246, 1987; Feuerstein, B. et al., Nuc. Acids Res. 17:6883-6892, 1989). This binding has been suggested to occur through interaction of the positively charged amine groups in the polyamine backbone and negatively charged sites on the DNA backbone. Because of the nature by which electrophilic chemotherapy drugs or oxygen radicals generated by radiotherapy attack helical B-DNA within cells, the ability of polyamines to bind DNA and disrupt normal B-DNA structure could be helpful in protecting DNA within cells to which a polyamine was delivered.

An additional strategy for protecting cells against electrophiles/radicals has been to augment levels of the naturally occurring cellular nucleophile, glutathione (GSH). Both animal and cell culture studies have shown that there is a direct relationship between the intracellular concentration of GSH and the amount of exogenously administered alkylating molecule that is needed to achieve cell kill (Ho, D. and Fahl, W., J. Biol. Chem. 259:11231-11235, 1984; Ellouk-Achard, S. et al., Arch. Toxicol. Suppl. 17:209-214, 1995). Efforts to exogenously administer GSH to cells as a protectant have failed because mammalian cells are generally unable to take up this nucleophile. There have been efforts to modify the GSH molecule to enable cellular uptake, but these have not found clinical use.

Amifostine (WR-2721), a small molecule amine containing a thiophosphate group that is presumably converted to a thiol in cells, has been used systemically as a radio- and chemoprotectant with mixed results. Though it may provide free —SH groups within cells, it is not known to contain activity as either a growth regulator or as a modifier of DNA structure.

Edwards et al. (U.S. Pat. No. 5,217,964 and U.S. Pat. No. 5,434,145) described the synthesis of short, spermidine- or spermine-like polyamine molecules that were modified to contain an alkyl-thiophosphate or alkyl-thiol group. In U.S. Pat. No. 5,217,964, the attached thiophosphate group (i.e., —$SPO_3H_2$) would require enzymatic activation by cellular phosphatases to form the nucleophilic —SH group. The alkyl-thiophosphate group(s) is bound to the polyamine molecule through a terminal benzyl ring and/or through one or more of the amines in the polyamine backbone. Polyamines containing aromatic rings have been described in the art to be structural inhibitors of the membrane polyamine transporter in mammalian cells and have been shown, themselves, not to be transported into cells. In U.S. Pat. No. 5,434,145, Edwards showed bonding of alkyl-thiophosphate or alkyl-thiol groups to one or more of the backbone amines that are present in the short polyamine molecules. By modifying the secondary amines in the polyamine backbone with alkyl-thiophosphate groups, the amines were converted to tertiary amines, and this markedly altered the basicity of the individual modified amine, as well as the overall polyamine molecule. The attenuated basicity of the individual amine groups was accompanied by an alteration in 3-dimensional structure at these sites. With added alkyl functionality on the amine nitrogen atoms, steric bulkiness increased, so the ability or freedom of the molecule to rotate and twist at these sites was markedly reduced. The altered basicity and steric constraints in these short spermine-like polyamines was surmised to perturb DNA binding by the polyamine as compared to their natural polyamine counterparts. Consistent with this (DNA binding is a biological activity of natural polyamines), Edwards provided no information regarding biological activity for any of the structures proposed in U.S. Pat. No. 5,217,964 or U.S. Pat. No. 5,434,145.

There is a need in the art, then, to create polyamine-based molecules that are optimized to achieve: i) local and transient growth regulation, ii) disruption of normal helical DNA structure upon binding, and iii) delivery and display of nucleophilic or other functional moieties within cells to enable scavenging of reactive electrophiles and radicals. There would be great advantage in developing polyamine derivatives that could be used topically to prevent or diminish the toxic side effects of cancer chemotherapy and radiotherapy.

SUMMARY OF THE INVENTION

The present invention provides novel polyamine compounds and pharmaceutical compositions for reducing or preventing toxic side effects of radiotherapy and cancer chemotherapeutic agents. The polyamine compounds of the invention are referred to herein as "chemoprotective polyamines."

One aspect of the invention features a compound of Formula I:

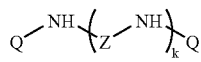

wherein:
each Z is independently A or $R^1$;
each A is independently:

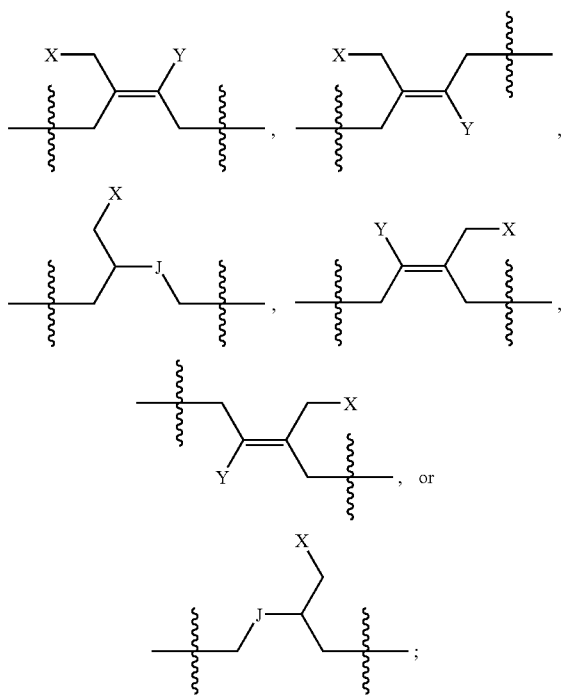

J is a single bond or —CH(Y)—;
X is D or —$R^2$-D;
Y is H, alkyl, or $R^3$-D;
D is —OH, —SH, —$SR^4$, or —$NR^4R^5$;
each $R^1$ is independently $C_{3-8}$ alkylene;
each $R^2$, $R^3$, $R^6$, and $R^7$ is independently $C_{1-6}$ alkylene;
$R^4$ is H or lower alkyl;
$R^5$ is H, lower alkyl, or —$R^6$-D;
Q is H, lower alkyl, or —$R^7$—$SR^4$;
k is an integer from 2 to about 16;
or a stereoisomer, prodrug, pharmaceutically acceptable salt, or mono or polyprotonated acid salt thereof.

In one embodiment, each A is independently:

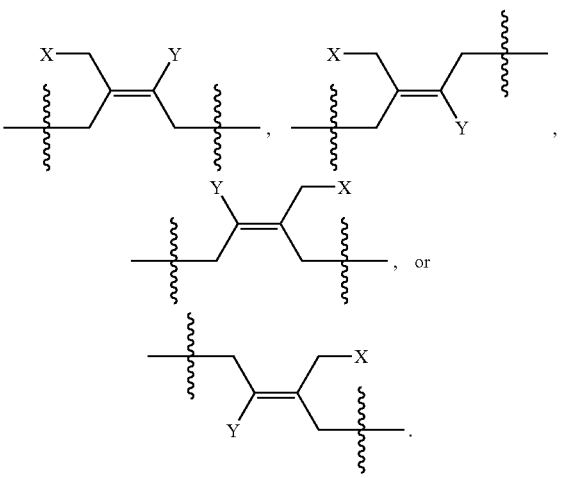

In this embodiment, Y may be H or $R^3$-D. X may be D or $R^2$-D. In this embodiment, k is an integer from 2 to about 16. In specific embodiments, k is 2, 3, 4, 5, 6, 7 or 8. In other specific embodiments, k is 2-8, each $R^1$ is butylene, X is D, D is —$NR^4R^5$, $R^4$ is H, and $R^5$ is ethyl, and Q is ethyl. In yet other specific embodiments, k is 2, 4, 6 or 8, each $R^1$ is butylene, X is D, D is —SH, and Q is ethyl. Yet another specific embodiment comprises a compound wherein k is 4, each $R^1$ is butylene, X is D, D is —$NR^4R^5$, $R^4$ is H, $R^5$ is methyl, and Q is ethyl. In other embodiments, Q is H or lower alkyl. Exemplary compounds having these features are shown in FIG. 1A through FIG. 1C.

In another embodiment, each A is independently:

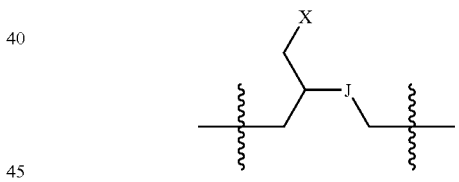

In this embodiment, Y may be H or $R^3$-D. X may be D or $R^2$-D. In this embodiment, k is an integer from 2 to about 16. In specific embodiments, k is 2, 3, 4, 5, 6, 7 or 8. Q may be H or lower alkyl. J is a single bond; in specific embodiments, J is —CH(Y)—. Exemplary compounds having the aforementioned features are shown in FIG. 1D and FIG. 1E.

Another aspect of the invention features a pharmaceutical preparation for reducing or preventing hair loss, dermatitis, mucositis or gastrointestinal distress caused by treatment with a chemotherapeutic agent or radiation therapy, which comprises at least one compound of Formula I as described above, and a topical delivery vehicle for locally delivering the compound to dermal or mucosal cells of skin, scalp, mouth, nasoesophageal, gastrointestinal or urogenital system. In certain embodiments, the pharmaceutical preparation further comprises at least one other agent that reduces or prevents hair loss, dermatitis, mucositis or gastrointestinal distress caused by treatment with a chemotherapeutic agent or radiation therapy, for instance, an anti-proliferative agent, a chemoprotective inducing agent or a free radical scavenger.

The topical delivery vehicle comprises one or more of liposomes, lipid droplet emulsions, oils, aqueous emulsions of polyoxyethylene ethers, aqueous alcohol mixtures, aqueous ethanol mixtures containing propylene glycol, aqueous ethanol mixtures containing phosphatidyl choline, lysophosphatidyl choline and triglycerides, xanthan gum in aqueous buffer, hydroxypropylmethylcellulose in aqueous buffer or aqueous alcohol mixtures, diethylene glycol monoethyl ether in aqueous buffer, and biodegradable microparticles.

In a specific embodiment, the pharmaceutical preparation is formulated for topical delivery to skin or hair follicles, and the delivery vehicle comprises an aqueous alcohol mixture and, optionally, propylene glycol. Preparations of this type may be formulated as creams, lotions, ointments or gels. In another specific embodiment, the pharmaceutical preparation is formulated for topical delivery to the oral cavity or nasoesophageal passages. In this embodiment the delivery vehicle preferably comprises a mucoadhesive substance. It may be formulated as an aerosol, oral rinse, ointment or gel. In yet another specific embodiment, the pharmaceutical preparation is formulated for vaginal or rectal delivery and comprises a mucoadhesive substance. These preparations may be formulated as creams, ointments, lotions, gels, foams or suppositories. In still another specific embodiment, the pharmaceutical preparation is formulated for topical delivery to the gastrointestinal tract and the delivery vehicle comprises one or more of nonionic liposomes and mucoadhesive substances. Preferably, the preparation is formulated as a liquid for coating the surface of the gastrointestinal tract.

According to another aspect of the invention, methods are provided for reducing or preventing hair loss dermatitis, mucositis or gastrointestinal distress in a patient undergoing treatment with a chemotherapeutic agent or radiation therapy. The methods comprise administering to the patient a pharmaceutical preparation as described above, in an amount and for a time sufficient to reduce or prevent the hair loss, dermatitis, mucositis or gastrointestinal distress. In one embodiment, the pharmaceutical preparation is administered beginning at least one day, and preferably up to five or more days, prior to chemotherapy or radiation therapy. In another embodiment, the pharmaceutical preparation is administered after initiation of chemotherapy or radiation therapy. Preferably, the pharmaceutical preparation is administered throughout a course of chemotherapy or radiation therapy and, in certain instances continues after termination of a course of chemotherapy or radiation therapy.

The aforementioned methods may further comprise administering to the patient at least one other agent that reduces or prevents hair loss, dermatitis, mucositis or gastrointestinal distress caused by treatment with a chemotherapeutic agent or radiation therapy. These other agents may include anti-proliferative agents, chemoprotective inducing agents or free radical scavengers, for instance.

The present invention also provides a method of treating cancer that increases a patient's tolerance to high doses of a chemotherapeutic agent or radiation therapy. The method comprises (a) administering the high dose of the chemotherapeutic agent or radiation therapy to the patient; and (b) administering one or more of the above-described pharmaceutical preparations for reducing or preventing one or more of chemotherapy- or radiation therapy-induced hair loss, dermatitis, mucositis or gastrointestinal distress, in an amount and for a time to reduce or prevent the one or more of the chemotherapy- or radiation therapy-induced hair loss, dermatitis, mucositis or gastrointestinal distress, thereby increasing the patient's tolerance to the high dose of the chemotherapeutic agent or radiation therapy.

Other features and advantages of the present invention will be understood by reference to the drawings, detailed description and examples that follow.

BRIEF DESCRIPTION OF THE DRAWINGS

FIG. 1A-FIG. 1E illustrate the structures of certain of the chemoprotective polyamine molecules whose synthetic pathways are illustrated in the reaction schemes. FIG. 1A shows compounds PrC 110, 111, 112 and 113, olefinic core displaying —NH—$CH_2$—$CH_3$ functional group; FIG. 1B shows compounds PrC 114, 115, 116, 117 and 118, olefinic core displaying —SH or —OH functional group; FIG. 1C shows compounds PrC 119, 120, 121, 122 and 123, olefinic core displaying —$NHCH_3$, —$N(CH_3)_2$ or —SH functional group; FIG. 1D shows compounds PrC 210, 211, 212, 213 and 214, aliphatic core displaying —OH, —SH, —$SCH_3$ or —$NHCH_2CH_3$ functional group; FIG. 1E shows compounds PrC 215, 216, 217 and 218, aliphatic core displaying —OH, —SH, —$SCH_3$ or —$SCH_2CH_2N(CH_3)_2$ functional group.

FIG. 3B shows that the induced p21 level is greater after a 30 hr exposure compared to a 50 hr exposure to drug. In these experiments, the 23SK human skin cells were exposed for 30 hr to an "IC80" dose of each of the indicated chemoprotective polyamines and then lysed. Cell extracts were then prepared in order to measure p21 levels by western analysis (FIG. 3A).

FIG. 5A shows results from untreated, exponentially growing 23SK cells. FIG. 5B shows, as a control treatment, results from incubation of cells in serum-free medium. FIG. 5C shows results from cells treated with PrC-117 for 72 hr. FIG. 5D shows results from cells treated with PrC-117 for 72 hr, then switched for 48 hr to medium devoid of the PrC-117 molecule.

DETAILED DESCRIPTION OF ILLUSTRATIVE EMBODIMENTS

Figure 1D:
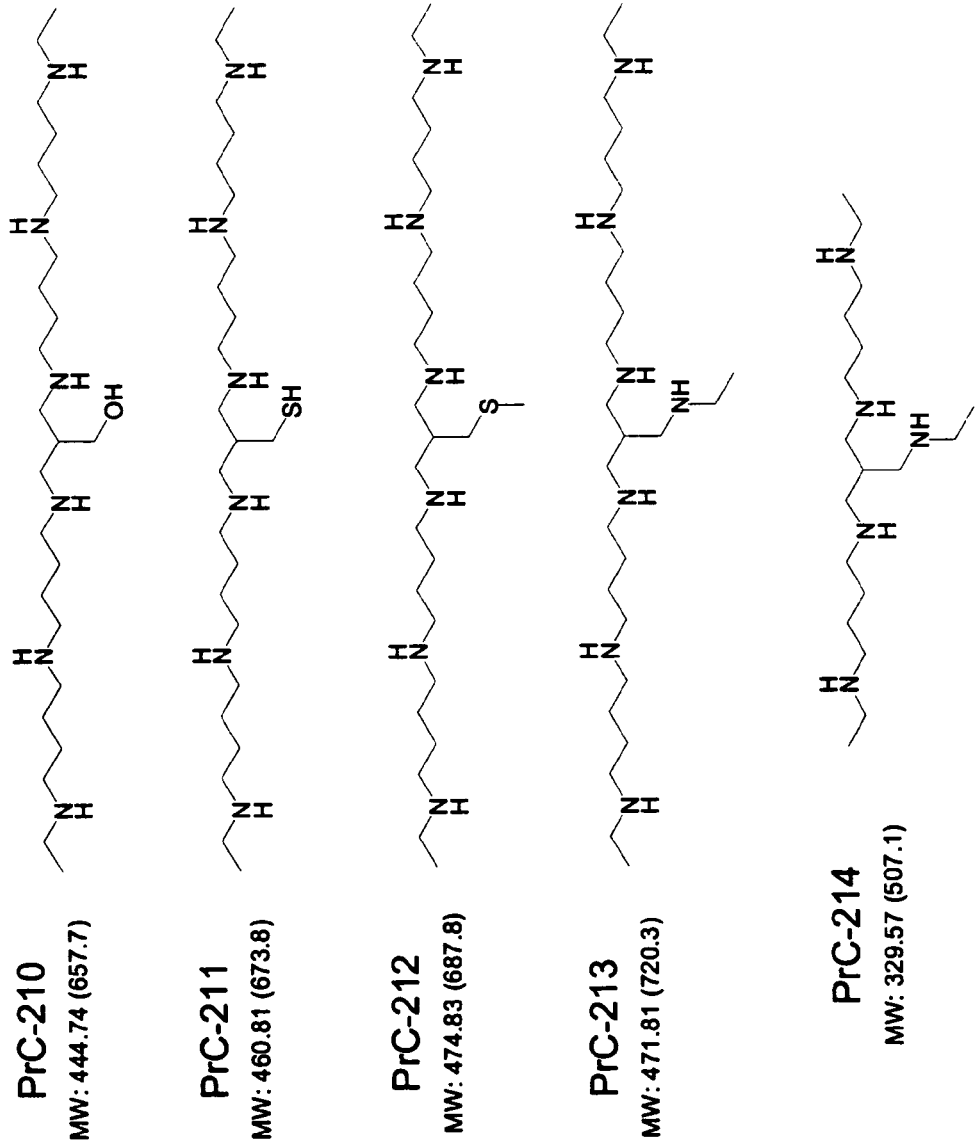

The present invention provides compounds for use in pharmaceutical preparations and methods for protecting non-cancerous, rapidly dividing cells in a patient's body from the toxic effects of chemotherapeutic agents or radiotherapy administered to the patient. In particular, the compositions and methods of the invention are designed for protecting epithelial cells. Most particularly, the targets are epithelial cells lining hair follicles and epithelial and/or mucosal cells of the skin, mouth, gastrointestinal (GI) and urogenital tract. In one embodiment, the compositions are used to reduce or prevent alopecia during cancer therapy, by topically applying the composition to the scalp. Another embodiment comprises reduction or prevention of gastrointestinal distress due to cancer therapy by administering the compositions orally. Another embodiment involves reducing or preventing mucositis from chemotherapy or radiotherapy by administering the compositions topically to the appropriate region of the body. In yet another embodiment, the compositions are used to prevent radiation-induced dermatitis, skin rash, and ulceration at the site of irradiation by applying them to the skin.

The chemotherapeutic agents from which protection of normal cells is desired may be one or a combination of agents used for such purpose, such as alkylating agents, antimetabolite inhibitors of DNA synthesis, antitumor antibiotics, mitotic spindle poisons, vinca alkaloids, and topisomerase inhibitors. Specific chemotherapeutic agents include, but are not limited to, altretamine, asparaginase, bleomycin, busulfan, carboplatin, cisplatin, carmustine, chlorambucil, cladribine, cyclophosphamide (cytoxan), cytarabine, dacarbazine, dactinomycin, daunorubicin, doxorubicin, etoposide, floxuridine, fludarabine phosphate, fluorouracil, hydroxyurea, idarubicin, ifosfamide, lomustine, mechlorethamine, nitrogen mustard, melphalan, mercaptopurine, methotrexate, mitomycin, mitoxantrone, paclitaxel, pentostatin, pliamycin, procarbazine, streptozocin, teniposide, thioguanine, thiotepa, vinblastine and vincristine. The radiation therapy consists of all useful types of radiation used in cancer treatment, including x-rays, gamma-rays, electron beams, photons, alpha-particles and neutrons.

Commonly-owned, co-pending U.S. application Ser. No. 10/214,917 and International Application No. PCT/US02/25216, each filed Aug. 7, 2002, describe that several types of known polyamines and polyamine analogs, referred to therein as "polyamine effector" compounds, can be efficiently delivered to the aforementioned target cell populations, where they are capable of protecting those cells from the harmful side effects of chemotherapy or radiotherapy. The present invention provides novel polyamine compounds specifically designed for improved efficacy in protecting normal cells from the detrimental effect of cancer chemotherapy or radiation therapy. These molecules are referred to herein as "chemoprotective polyamines."

Certain definitions that will assist in the understanding of the present invention are set forth below, while others are provided throughout the specification. With respect to the compounds of the invention, it should be noted that if any variable occurs more than one time in any constituent or in any formula, its definition in each occurrence is independent of its definition at every other occurrence. Thus, for example, if a compound of the present invention is shown to incorporate, for example, one or more of $R^1$, $R^2$, $R^3$, $R^4$, $R^5$, $R^6$, $R^7$, —OH, —SH, —$SR^4$, or —$NR^4R^5$, then the $R^1$, $R^2$, $R^3$, $R^4$, $R^5$, $R^6$, $R^7$, —OH, —SH, —$SR^4$, or —$NR^4R^5$ at each occurrence is selected independently. Combinations of $R^1$, $R^2$, $R^3$, $R^4$, $R^5$, $R^6$, $R^7$, —OH, —SH, —$SR^4$, or —$NR^4R^5$ are permissible only if such combinations result in stable compounds.

Polyamines are small aliphatic amines found in all living cells. By nature, polyamines within cells are polycationic (i.e., capable of sustaining or neutralizing one or more equivalents of acid). They are biosynthesized from amino acids, such as arginine and ornithine. Examples of common polyamines found in plant and animal cells are: putrescine ($NH_2(CH_2)_3NH_2$), formed by the decarboxylation of ornithine or arginine; spermidine ($NH_2(CH_2)_3NH(CH_2)_4NH_2$); and spermine ($NH_2(CH_2)_3NH(CH_2)_4HN(CH2)_3NH_2$); the latter two being formed by subsequent addition of an aminopropyl moiety to putrescine and spermidine, respectively. Because such polyamines are found in nature, they may be referred to as "naturally-occurring" polyamines. However, they may be prepared by a variety of synthetic strategies, as would be known in the chemical arts.

The term "polyamine analogs" as used herein refers to polycationic molecules that are similar, but not identical to polyamines found in nature. Polyamine analogs may be branched or unbranched, or may have other structural variations as compared to naturally-occurring polyamines, while retaining the central features of polyamines (multiple amine groups, polycationic within cells). Polyamine analogs may be further categorized into three groups: (1) simple polyamine analogs, (2) constrained or conformationally restricted polyamine analogs, and (3) linked or long-chain polyamine analogs.

A "simple polyamine analog" retains the flexibility conferred by the aliphatic carbon backbone, as well as the approximate carbon chain length of naturally-occurring polyamines, but possess a modification or contain one or more added functional groups (e.g., sulfhydryl, phenyl, alkyl) that confers a desired feature or advantage to the molecule.

By comparison, "conformationally restricted polyamine analogs" (sometimes referred to herein as "constrained polyamine analogs" are modified in their carbon backbone to remove flexibility in the modified area, such that two or more amino functionalities in the molecule are restricted to a particular spatial location. Such modification often is accomplished by introducing a cyclic or unsaturated moiety at one or more locations in the carbon backbone, as described in greater detail herein.

"Linked or long-chain polyamine analogs" are polyamines that are longer than naturally-occurring polyamines such as spermine. Increasing the overall length of a polyamine may be accomplished, for example, by linking together oligoamines or by adding oligoamine "units" (such as aminopropyl or aminobutyl groups) to a foundation molecule, such as spermine. Thus, while spermine has a 3-4-3 carbon backbone (4 carbons between the two internal amino groups and 3 carbons between each internal amino group and the respective terminal amino groups), linked or long-chain analogs might comprise an additional one, two, three, four or more aminopropyl or aminobutyl groups, for example, on either or both ends of the molecule, and further may comprise terminal methyl or ethyl groups on either or both ends.

As used herein, the term "antiproliferative" refers to an agent that slows or stops cell division. The antiproliferative agent may exert its effect by inhibiting cell cycle progression at one or more stages. Such an agent may be referred to herein as a "cell cycle progression inhibitor." The chemoprotective polyamines of the invention can act as antiproliferatives, specifically cell cycle progression inhibitors, by associating with and modifying the conformation or structure of DNA. These agents are sometimes referred to herein as "DNA modifiers."

The design of the chemoprotective polyamines of the present invention emerges from the inventors' appreciation of the advantages associated with blending certain important chemical properties within a single multifunctional molecule, 1) molecular structure necessary for efficient binding to DNA and, in some instances, modification of the conformation or structure of DNA; 2) nucleophilic reactivity, to trap electrophilic chemicals that can challenge the integrity of helical DNA; and/or 3) free radical-scavenging activity to reduce or eliminate free radicals often generated by irradiation or various chemotherapeutic agents (e.g., certain reactive oxygen species).

In regard to structure, the ability of a polyamine to physically align closely, or "dock" with DNA should be maintained. Mimicking the general linear nature of the known natural polyamines enables the chemoprotective polyamines of the invention to maintain DNA binding ability. Another important feature common to natural polyamines is the presence of multiple secondary amine nitrogen atoms throughout the backbone. These atoms are known to be protonated, and thus positively charged, at physiologic pH. Accordingly, maintaining secondary amine functionality throughout a chemoprotective polyamine further provides sufficient active binding sites.

Nucleophilic and/or free radical-scavenging activity was designed into the chemoprotective polyamines with the aim of maintaining all of the above mentioned structural and binding features. In various exemplary embodiments described herein, electron-rich groups, bearing sp3-hybridized nitrogen, sulfur or oxygen atoms, were positioned strategically within the polyamine backbone so that overall linearity and secondary amine character would be preserved for efficient DNA binding. The enhanced reactivity of allylic functional groups, compared to their alkyl counterparts, was also considered in designing placement of functional groups in certain embodiments. In some embodiments, chemoprotective polyamines with an olefinic core have the nucleophiles/scavengers positioned on allylic positions specifically to enhance the reactivity of those functional groups. In these embodiments, the core segment bearing the functional group was restricted in size, consistent with natural polyamine features, and provides a suitable platform from which the nucleophile or other functional group is displayed. This design feature allows one side, or face, of the 3-dimensional polyamine structure to interact with DNA while the other face, bearing the reactive functional group, is projected away from the DNA, sterically unencumbered, thus free to react with toxic electrophilic chemicals or free radicals present in the cellular matrix.

The chemoprotective polyamines of the present invention are represented by the general structure of Formula I:

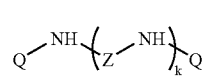

I

In Formula I, "Z" is either "A" or "$R^1$." "A" represents a "core" segment and the $R^1$ and Q groups typically represent alkylene ($R^1$) or alkyl (Q) chains of varying length (branched or unbranched), which, together with the amine groups as shown, make up the linked oligoamine segments that form the polyamines of the present invention.

As used herein, "alkylene" refers to a bivalent alkyl radical having the general formula —$(CH_2)_n$—, where n is 1 to about 8. Non-limiting examples include methylene, ethylene, trimethylene, butylene, pentamethylene, and hexamethylene. Alkylene groups may be branched or unbranched. Alkylene groups may also contain one or more double or triple bonds within the backbone of the —$(CH_2)_n$— moiety, provided that the resultant compound is stable. Non-limiting examples include —$CH_2$—C≡C—$CH_2$— and —$CH_2$—CH═CH—$CH_2$—. Alkylene groups can be substituted or unsubstituted, provided that the resultant compound is stable and so long as the substituent does not substantially interfere with present compound's intended mode of action. In certain circumstances, alkylene is preferably $C_{3-8}$ alkylene, while in other circumstances, even within the same molecule, alkylene is preferably $C_{1-6}$ alkylene.

As used herein, "alkyl" refers to a saturated straight or branched hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl, octyl, decyl, dodecyl, octadecanyl, and eicosanyl.

The core segment ("A") functions in two ways: (1) it presents a platform for display of a protective functional group, namely a nucleophile or a free radical scavenger; and (2) it may be designed to introduce a conformational constraint to the polyamine (e.g., a double bond or a cyclic structure). The linked oligoamine segments (sometimes referred to as "arms" or as "polyamine side chains") function to enable the molecule to "dock" with DNA, as do naturally occurring polyamines. In one embodiment, a compound of the invention comprises one core and an "arm" of varying length on either side of the core. In another embodiment, the core may have a single arm (i.e., the core group is at one end or the other of the polyamine molecule). In another embodiment, the chemoprotective polyamine comprises two or more cores (which may be the same or different), which can be side-by-side or separated by an oligoamine segment of varying length.

The core segment provides the molecule with conformational restraint and/or a protective functional group that is attached ("tethered") to the molecule in such a way as to be optimally available for interaction with electrophilic groups, free radical groups and other reactive species present on or generated by chemotherapeutic agents or radiation. In the present invention, conformation restraint is typically introduced through the use of a double bond between two carbons. As would be appreciated by those of skill in the art, other means of introducing conformational restraint include triple bonds and ring structures, such as three-, four-, five- and six-carbon or more substituted or unsubstituted rings (in the latter embodiments, with the proviso that the ring does not introduce bulk or steric hindrance that reduces the ability of the functional group to access its targets).

The protective functional groups displayed on the core are designed to act as nucleophiles or as free radical scavengers/antioxidants, with the understanding that certain functional groups may carry out both functions. Functional groups that typically act as nucleophiles, but that may also act as antioxidants or free radical scavengers, include, but are not limited to, —OH, —$NH_2$, —NHR, $NR_2$, —SH and —SR(wherein R is methyl or a lower alkyl which itself may be substituted with —OH, —$NH_2$, —NHR, $NR_2$, —SH or —SR).

The total length or size of a chemoprotective polyamine of the invention is generally described herein by the number of oligoamine segments ($R^1$—NH—) that make up the molecule. Typically the compounds comprise two or more such segments, and may comprise 3, 4, 5, 6, 7, 8, 9, 10, 11, 12, 13, 14, 15, 16 or even more such segments. The overall upper limit to length of the compounds is typically selected on the basis of practical considerations such as cost and ease of synthesis, solubility and/or skin or mucosal permeability, as measured against efficacy of the compound in exerting its protective effect within the cell. In specific embodiments, the chemoprotective polyamine comprises 2, 3, 4, 5, 6, 7 or 8 oligoamine segments.

1. Synthesis of Chemoprotective Polyamines Comprising Nucleophilic Cores

The synthetic approaches illustrated below demonstrate versatility regarding the choice of nucleophile incorporated into the core segments, the availability of both cis- and trans-isomers of the olefinic core and variability in the amine side chain segment length as well as number of segments desired.

Several reaction schemes and tables are presented throughout the sections below, with both reaction intermediates and final products being assigned unique descriptive numbers. Specific descriptions of the synthesis of the key molecules are set forth in Example 1.

1.1 Amine Side Chains

In exemplary embodiments of the invention, amine side chains were synthesized using the reaction sequences in Scheme 1. Primary alkyl amine 1 was converted to mesitylene sulfonamide 2, which was alkylated to provide N-phthaloyl protected 3. It should be noted that the segment length can be adjusted from two carbons to six carbons in this sequence of steps, and this invention is not limited to the four-carbon chain length of molecule 3. Deprotection of the terminal nitrogen gave 4, which was readily converted to 5. The bis-sulfonamide 5 represents the shortest amine side chain with regard to number of segments. Molecule 5 also was used for chain elongation by adding segments. The three reaction steps that convert 2 to 5 were repeated and therefore represent an iterative process by which 5 was converted to 8, 8 elaborated to 11 and 11 to 14. Each of the mesitylenesulfonyl protected amine side chains 5, 8, 11, 14, and related chain-extended derivatives, are suitable for attachment to a core segment. In sum, Scheme 1 describes how a single polyamine side chain may be produced. This process can be repeated to add additional polyamine side chain segments.

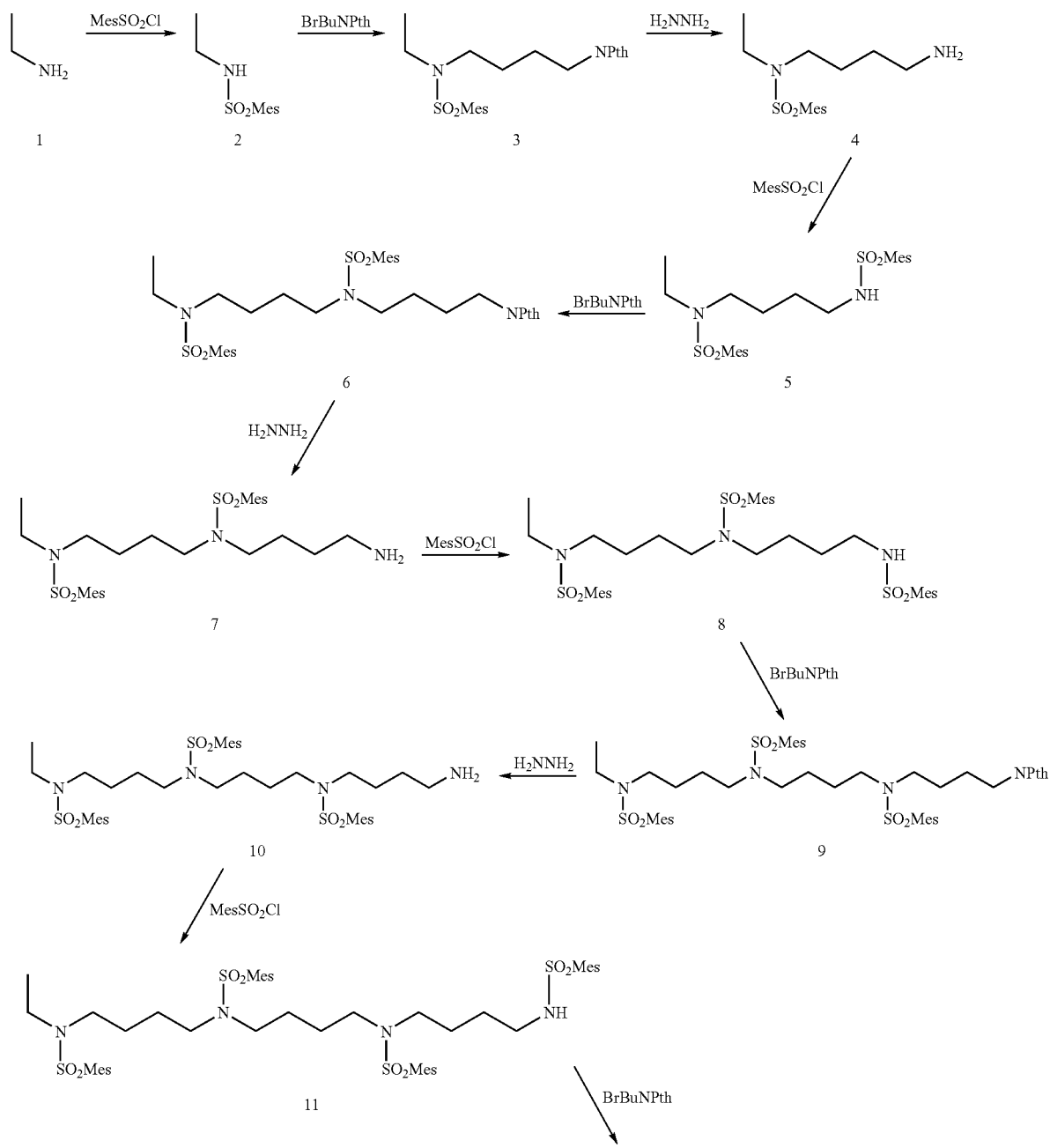

Scheme 1 - Polyamine Side Chain Synthesis

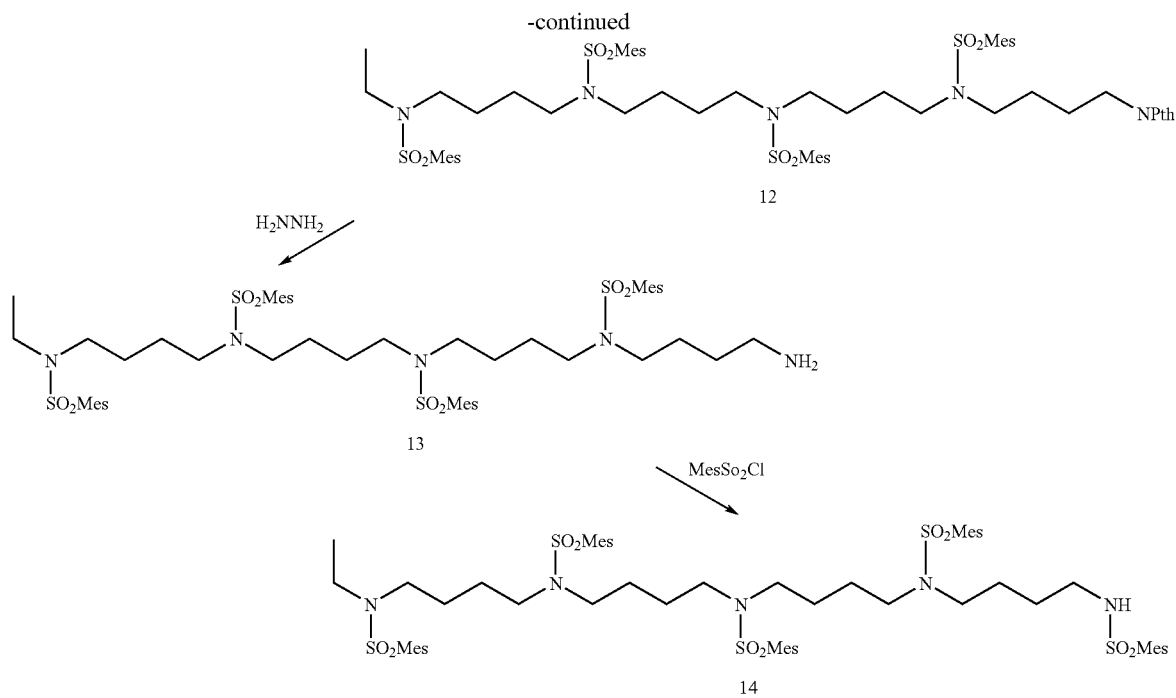

1.2 Synthesis of Olefinic Core and Side Chain Attachment

A general description of the olefinic core synthesis is illustrated in Scheme 2. Dihydroxyacetone dimer 15 was converted to ketone 16. Olefination of 16 provided ester 17, which was carefully reduced to the allylic alcohol 18 while maintaining the integrity of the silyl groups. Mesylation gave allylic mesylate 19, which was coupled to an amine side chain to provide 20, where A represents the mesitylenesulfonyl protected amine side chain. Acid treatment of 20 gave diol 21, which was monobenzoylated to provide 22. It should be noted that the cis- and trans-isomers of alcohol 22 can be separated by chromatography to provide the individual purified isomers. Alcohol 22 was then transformed to the allylic bromide 23, which was coupled to a second protected amine side chain to produce 24. For the purpose of this invention it should be noted that in 24, protected amine side chains A and A' can be identical, but can also vary in segment length as well as overall chain length. Hydrolysis of 24 gave mesitylenesulfonyl protected polyamine 25. Protected polyamine 25 can be deprotected (see polyamine 27 in Scheme 3), or serve as a versatile intermediate that can be further elaborated at the allylic alcohol position to insert alternative protective functional groups.

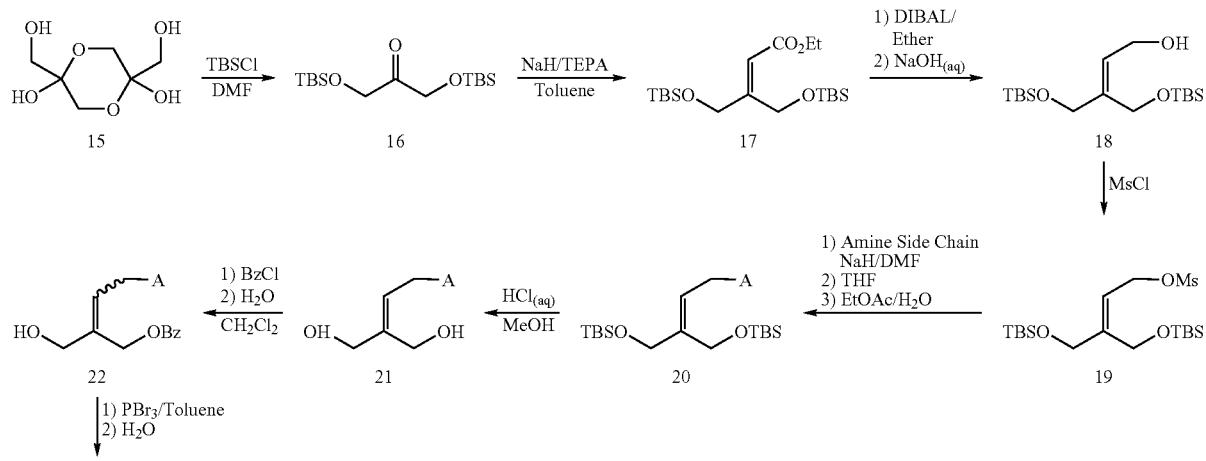

Scheme 2

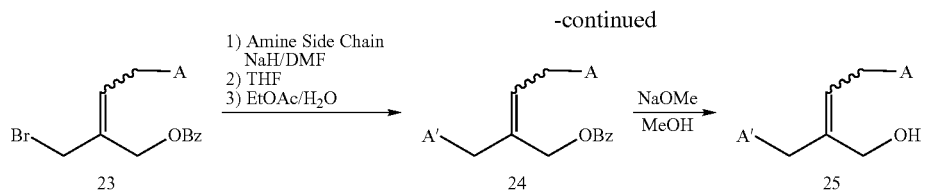

where A or A' are SO$_2$Mes protected polyamine side chains described in scheme 1.
where R or R' are the free polyamine side chains with the protecting groups removed.

1.3 Functional Groups on the Chemoprotective Polyamine Core

A method for introducing various protective functional groups onto a core segment is shown in Scheme 3. Alcohol 26 was converted to mesylate 27, which was subsequently reacted with various species having suitable nucleophilic character, to provide, for example, 29, 31, 33 or 35. Subsequent deprotection produced, for example, the chemoprotective polyamines 30, 32, 34 and 36.

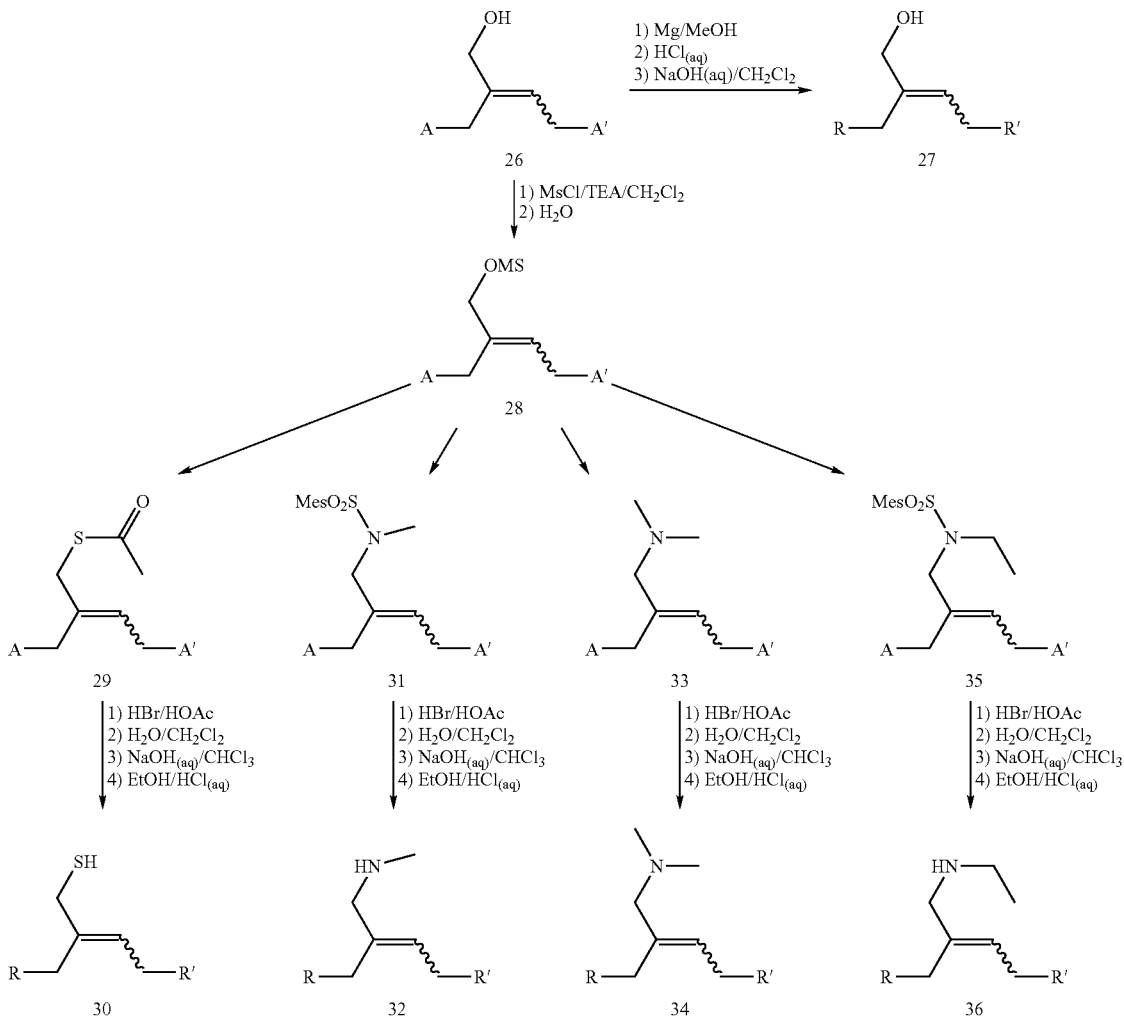

where A or A' are SO$_2$Mes protected polyamine side chains described in scheme 1.
where R or R' are the free polyamine side chains with the protecting groups removed.

1.4 Functional Groups Displayed from an Aliphatic Core

A synthetic approach to chemoprotective polyamines bearing functional groups on an aliphatic core segment is shown in Scheme 4.

change the growth regulation "phenotype" that would be linked with the displayed nucleophile "phenotype" on a particular chemoprotective polyamine. This combination of functions within a given molecule may be optimized for each

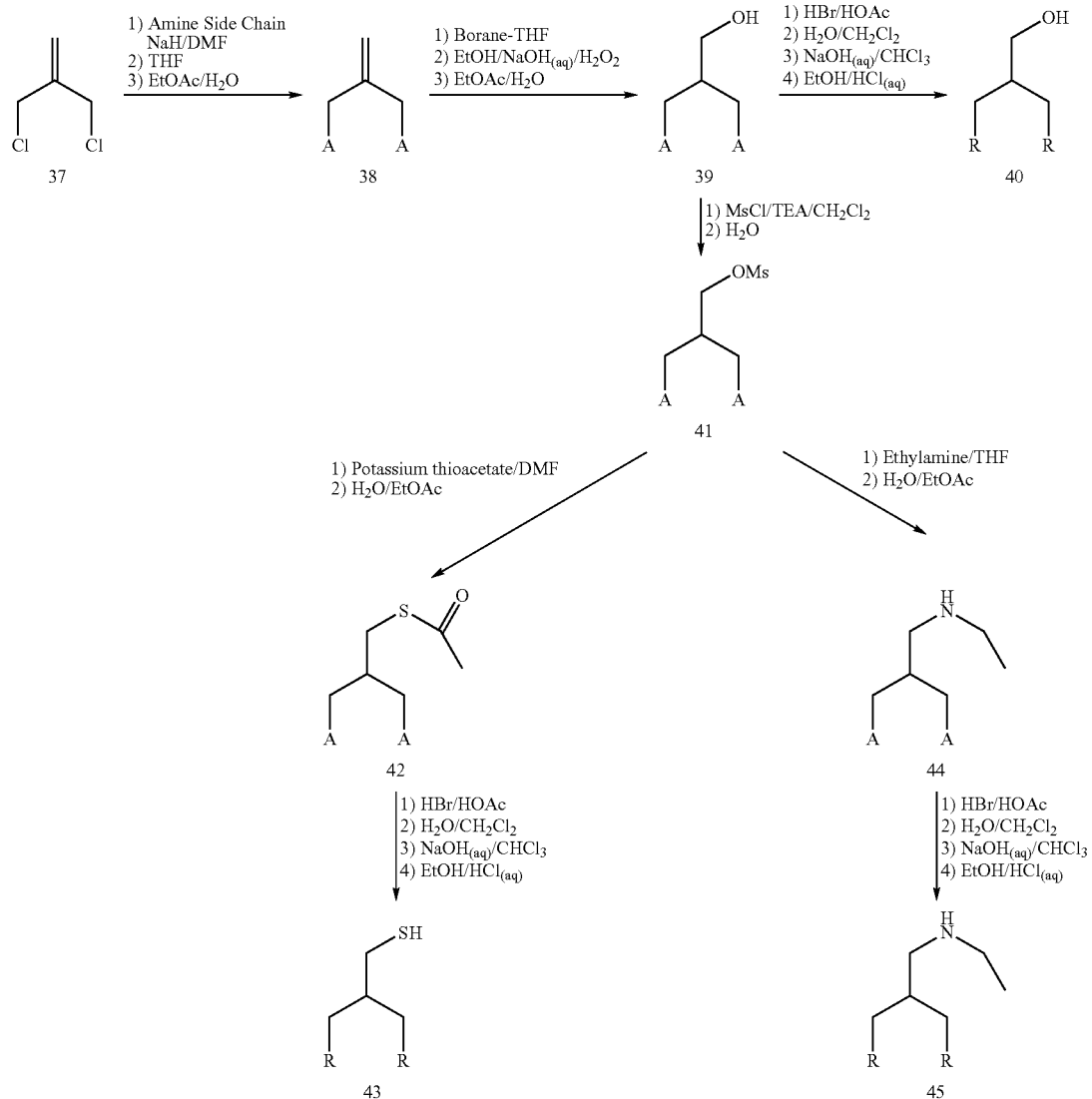

where A or A' are SO$_2$Mes protected polyamine side chains described in scheme 1.
where R or R' are the free polyamine side chains with the protecting groups removed.

In some pharmacologic settings, there may be advantage in displaying a protective functional group from a flexible aliphatic core as has been done in molecules PrC-210, PrC-211, as well as the rest of the molecules shown in FIG. 1D and 1E. Using chemoprotective polyamines to deliver nucleophiles/free radical scavengers to at-risk cells, while also binding DNA to enable DNA protection and growth regulation, requires optimization of each of the chemoprotective polyamine's structural parameters, including segment length, overall length, functional group, and the platform from which the functional group is displayed. For instance, displaying an alkyl-nucleophile side chain from a flexible core may change the interaction between polyamine and DNA, and with it, pharmacologic use of chemoprotective polyamines. In the reaction sequence of Scheme 4, dichloride 37 was converted to olefin 38, which was subsequently transformed to alcohol 39. Alcohol 39 can be deprotected to give 40, or converted to the mesylate intermediate 41. Mesylate 41 was then converted, with suitable nucleophiles, to 42 and 44, which upon deprotection, produce chemoprotective polyamines 43 and 45.

Other aliphatic polyamines may be prepared by hydrogenating olefinic polyamines of the invention. This is accomplished by employing hydrogenation catalysts in the presence of hydrogen or molecules that provide hydrogen during the course of a reaction, such as for example, hydrazine, cyclohexadiene, or alpha-terpinene. Further, as one ordinarily skilled in the art would recognize, one or more of the double bonds in any given olefinic polyamine may be selectively hydrogenated by selection of catalysts that preferably coordinate to one or more of the "D" moieties of the present compounds and transfer hydrogen selectively to the olefin adjacent to the "D" moiety. For a general overview, see J. March, Advanced Organic Chemistry: Reactions, Mechanisms, and Structure, Fourth Edition, John Wiley and Sons, New York (1992), pp 771-780.

1.5 Polyamines Containing Two or More Cores

The synthesis of a chemoprotective polyamine with more than one core unit is illustrated in Scheme 5. The core intermediate 23 (see Scheme 2) is reacted with sulfonamide 54 to give 55. Removal of the phthaloyl group provides 56, which upon sufonylation gives bis-sulfonamide 57. If the desired functional group on the core segments of the target polyamine is hydroxyl, 57 can be converted directly to silyl ether 60, where X=OH. Alternatively, the nucleophile can be modified by converting 57 to 58, followed by functional group transformation to 59. Sulfonamide 59 can likewise be converted to 60. Desilylation to 61, and subsequent benzoylation, gives 62. Conversion to the bromide 63 provides a pivitol intermediate. The chain-elongation process can be terminated by attaching an amine side chain, thus providing a polyamine bearing two core units. Alternatively, bromide 63 can be subjected to an iterative process that involves repeating the steps shown at the start of Scheme 5. This will install a third linker-core repeating unit in the polyamine chain. Manipulation of the functional group in a second or third core unit can be effected as shown in the conversion of 57 to 59.

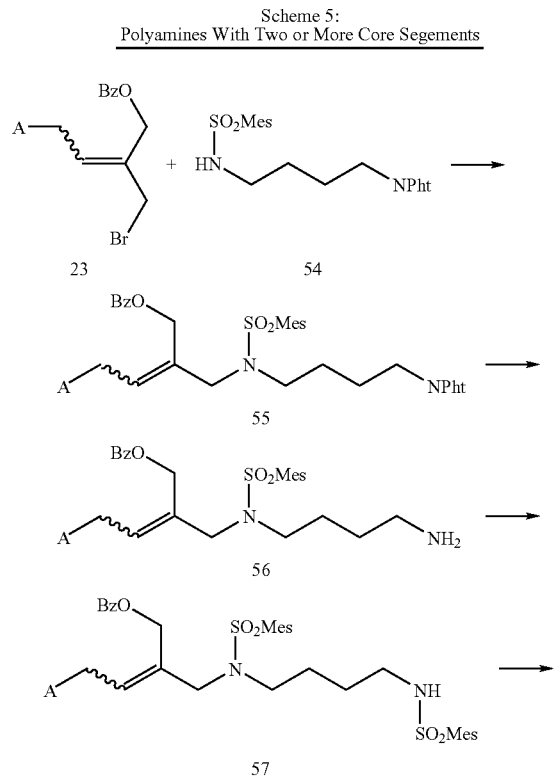

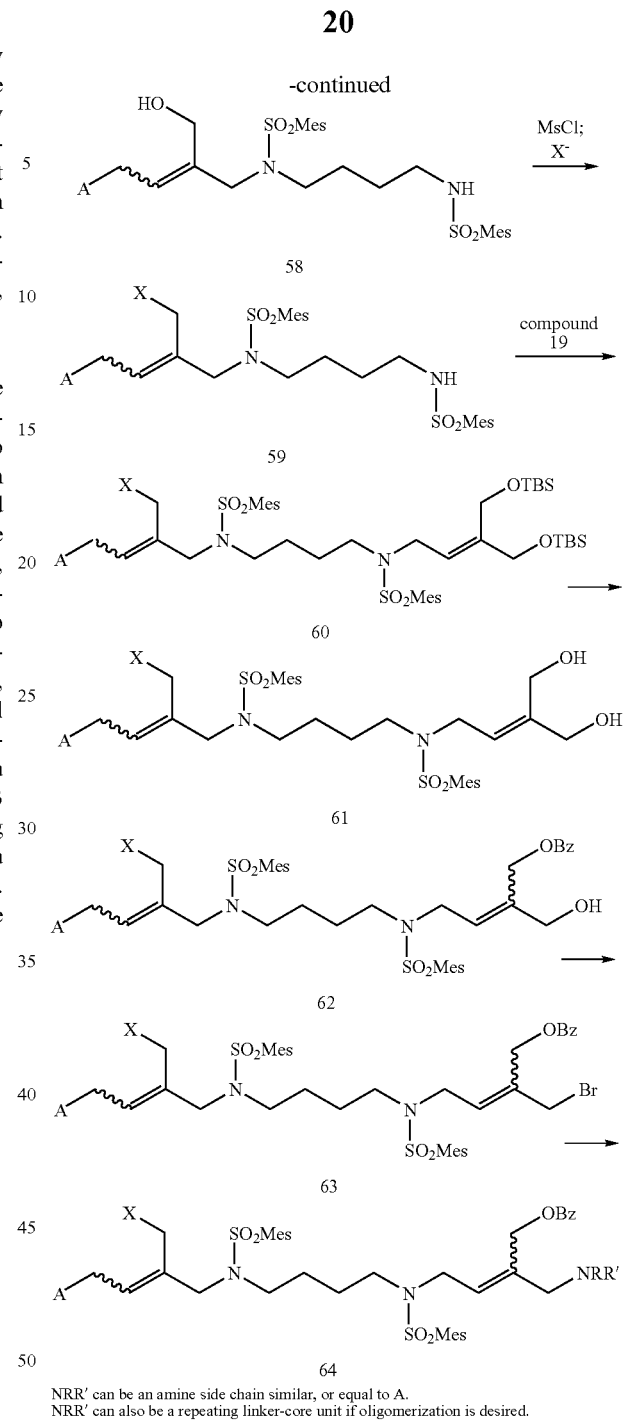

NRR' can be an amine side chain similar, or equal to A.
NRR' can also be a repeating linker-core unit if oligomerization is desired.

2. Utility of Chemoprotective Polyamines in Regulating Cell Growth and Protecting Against Cancer Therapies To determine the activity of the described compounds as regulators of cell growth, as well as to provide mechanistic insight into ways by which these compounds regulate cell growth, we examined chemical interaction between the subject compounds and nucleic acids and assessed the extent to which these chemical and growth regulatory properties conferred protection in animal tissues against cancer chemotherapy and radiotherapy. Several exemplary compounds of the invention were tested using various in vitro and in vivo model systems. The subject compounds were found to inhibit growth of human skin cells at sub-micromolar to millimolar concentrations, in a manner that could be correlated to their chemical structure. Consistent with this inhibition of cell growth, the compounds were shown to bind avidly to helical DNA, to induce expression of the negative growth regulator, p21, and to block cells within the G1 phase of the cell cycle, also in a manner related to their structure. When the subject molecules were applied locally by topical administration to rodent skin, they protected the hair follicle cells and blocked the alopecia normally seen following systemic administration of a chemotherapy drug.

The in vitro growth inhibitory effects of certain of the chemoprotective polyamines of the invention were measured using primary, diploid fibroblasts isolated from human skin. As shown in Table 1, $IC_{50}$ concentrations (the drug concentration that caused a 50% inhibition of cell growth) for the polyamines ranged from sub-micromolar to millimolar.

TABLE 1

| Compound # | [MW:HCl salt] | Expt. 1, $IC_{50}$ (uM) | Expt. 2 |
|---|---|---|---|
| PrC-110 | [523.9] | 1680 | 809 |
| PrC-111 | [739.0] | 980 | 180 |
| PrC-112 | [954.2] | 2.53 | |
| PrC-113 | [1169.3] | 0.33 | 0.21 |
| PrC-114 | [476.4] | 850 | 240 |
| PrC-115 | [691.6] | 4100 | 1090 |
| PrC-116 | [906.7] | 5.8 | |
| PrC-117 | [1121.9] | 0.32 | 0.24 |
| PrC-118 | [675.5] | 78 | |
| PrC-119 | [725.0] | 470 | 202 |
| PrC-120 | [1155.3] | 0.22 | 0.18 |
| PrC-121 | [1169.3] | 0.15 | |
| PrC-122 | [940.2] | 0.81 | |

Figure 2:
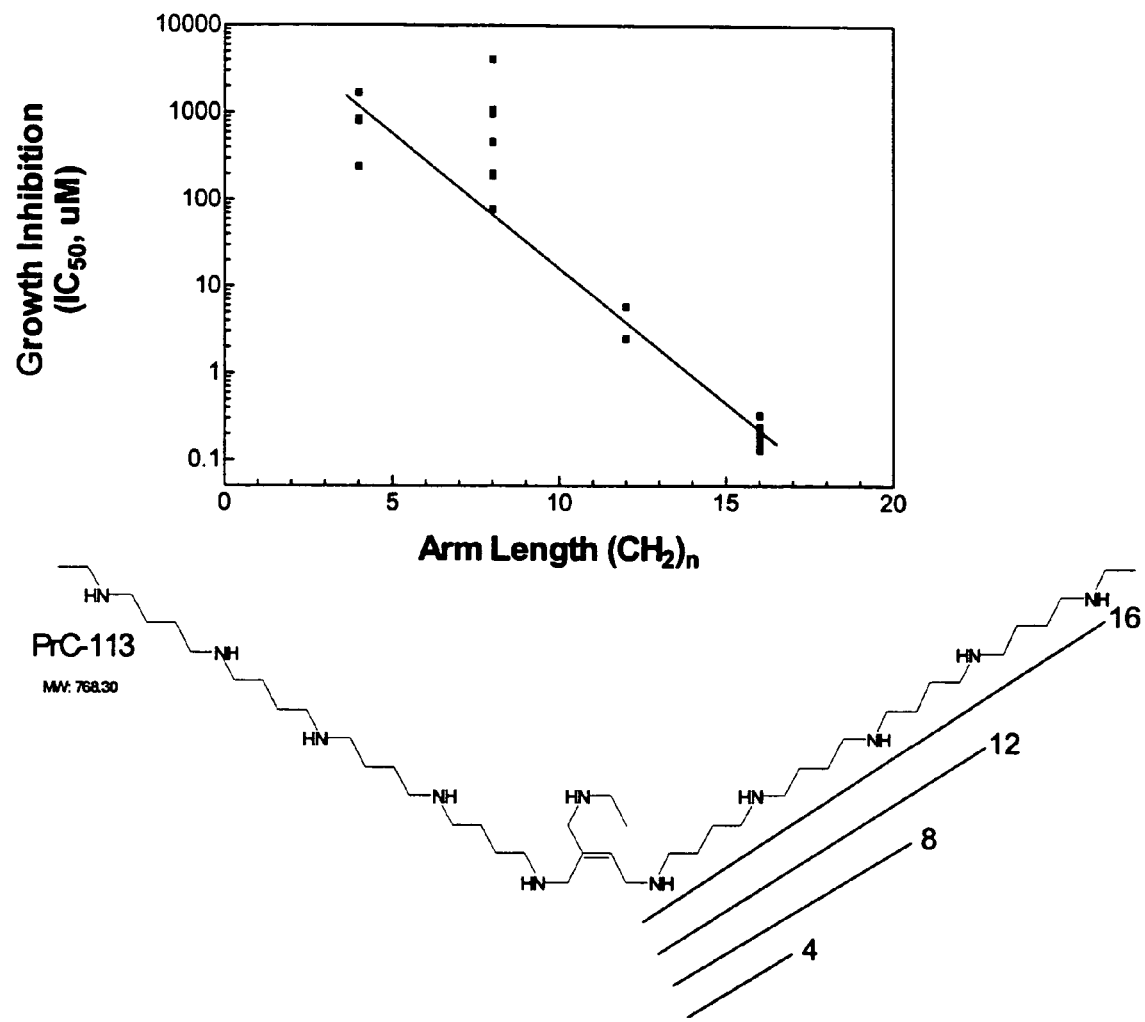
FIG. 2 illustrates the relationship between the number of aliphatic carbon atoms in each chemoprotective polyamine side chain ('arm') and the respective $IC_{50}$ dose for inhibition of human fibroblast growth.

As part of this invention, heretofore not described in the literature, FIG. 2 shows that the $IC_{50}$ concentration for each chemoprotective polyamine was tightly correlated with the length of the polyamine side chains ('arms') attached to a central butene core, with the long arms, i.e., those containing 16 aliphatic carbon atoms, associated with sub-micromolar $IC_{50}$ values.

The chemoprotective polyamines of the invention are also able to bind, denature and precipitate DNA from solution. As is known in the field, as the concentration of polyamine is increased, there is a point where polyamine binding to helical B-DNA induces single-stranded 'bubbles' and conversion to other forms of DNA structure, such as Z-DNA (Feuerstein, B. et al. Nuc. Acids Res. 17:6883-6892, 1989; Basu, H. and Marton, L. Biochem. J. 244:243-246, 1987), as well as precipitating the DNA from solution. Table 2 shows that the four molecules that contain '16 carbon arms,' i.e., PrC-113, PrC-117, PrC-120 and PrC-121, all have $IC_{50}$ concentrations that are lower than all of the other molecules that contain shorter aliphatic arms.

TABLE 2

| Compound # | [MW:HCl salt] | DNA Bind/ppt. Expt. 1, $IC_{50}$ (uM) | Expt. 2 |
|---|---|---|---|
| PrC-110 | [523.9] | 270 | |
| PrC-111 | [739.0] | 88 | |
| PrC-112 | [954.2] | 93 | |
| PrC-113 | [1169.3] | 35 | |
| PrC-114 | [476.4] | 94 | |
| PrC-115 | [691.6] | 37, | 83 |
| PrC-116 | [906.7] | 82, | 63 |

TABLE 2-continued

| Compound # | [MW:HCl salt] | DNA Bind/ppt. Expt. 1, $IC_{50}$ (uM) | Expt. 2 |
|---|---|---|---|
| PrC-117 | [1121.9] | 58, | 57 |
| PrC-118 | [675.5] | — | |
| PrC-119 | [725.0] | 89 | |
| PrC-120 | [1155.3] | 57 | |
| PrC-121 | [1169.3] | 49 | |
| PrC-122 | [940.2] | 102 | |
| PrC-123 | [906.7] | 131, | 117 |
| Spermine | | 2600 | |

This relationship between arm length of the chemoprotective polyamine and increased ability to disrupt and denature B-DNA structure is also a unique aspect of this invention. The increased ability to bind DNA and disrupt its helical structure may also contribute to the molecule's ability to protect cellular DNA against electrophilic chemotherapy drug metabolites and against oxygen free radicals generated during radiotherapy. Both of these toxic modalities are believed to require normal B-DNA helical structure within the cell's nuclear DNA in order to achieve chemical or physical disruption of the cellular DNA, the first step in the apoptotic cascade.

Figure 3A:
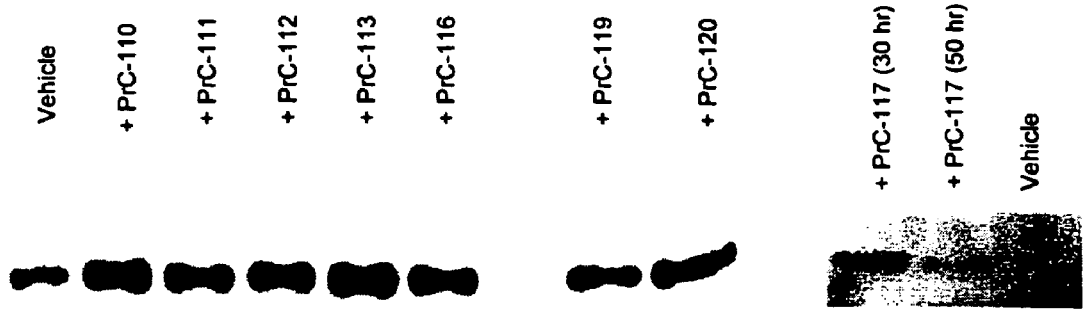
FIGS. 3A and 3B illustrate the level of induced p21 protein seen in diploid human fibroblasts after a 30 hr exposure to each of the indicated chemoprotective polyamines.
Figure 3B:
Figure 3B:
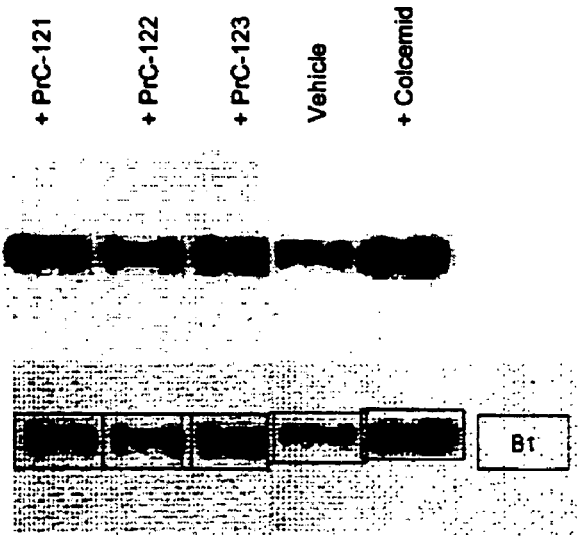
Figure 4:
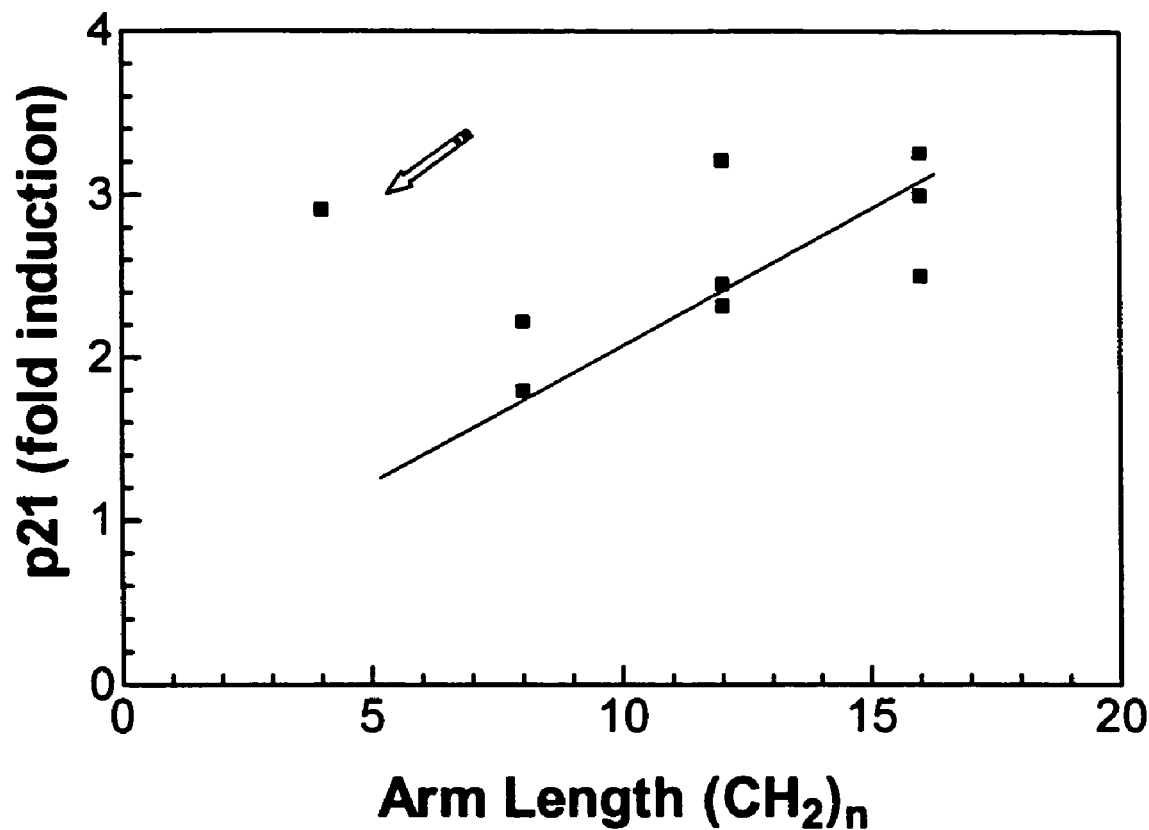
FIG. 4 illustrates the relationship between the number of aliphatic carbon atoms in each chemoprotective polyamine 'arm' and the respective induced p21 level in diploid human fibroblasts after a 30 hr exposure. The arrow points to the value for PrC-110, which also showed excellent efficacy in the in vivo alopecia test.
Figure 5A:
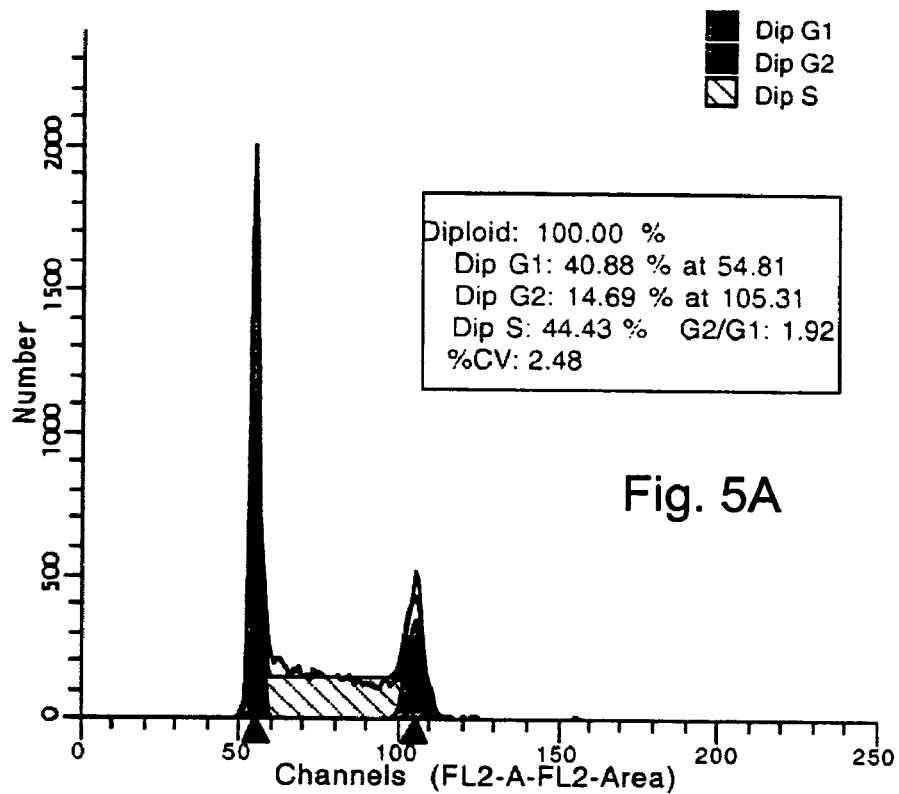
FIGS. 5A-5D are cell histograms showing the results from flow cytometry analysis of chemoprotective polyamine-treated 23SK skin cells.
Figure 5B:
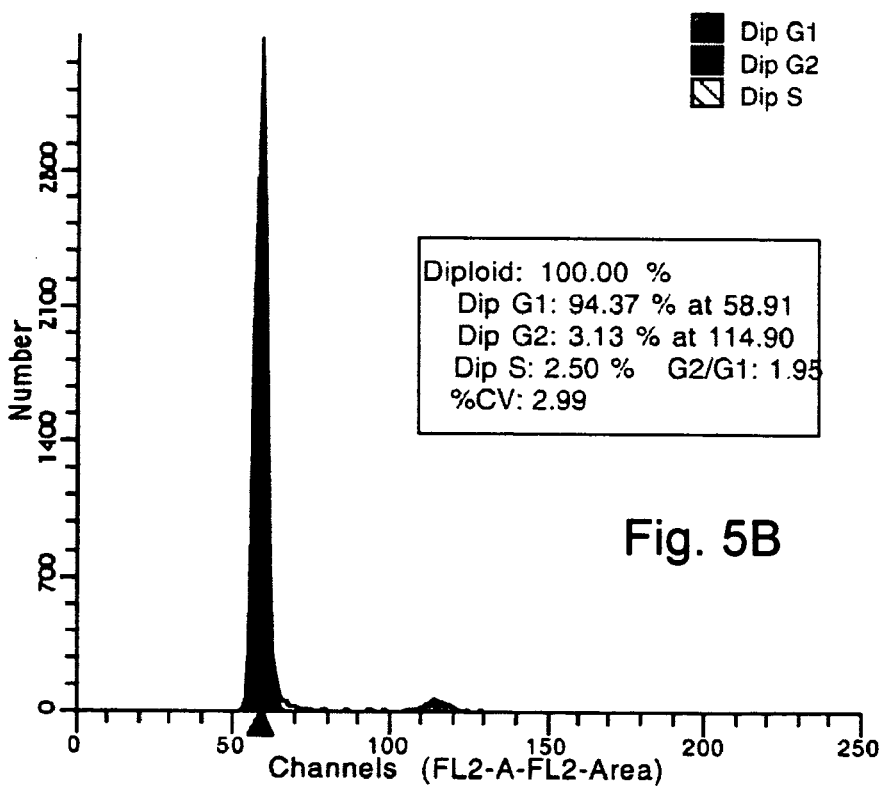
Figure 5C:
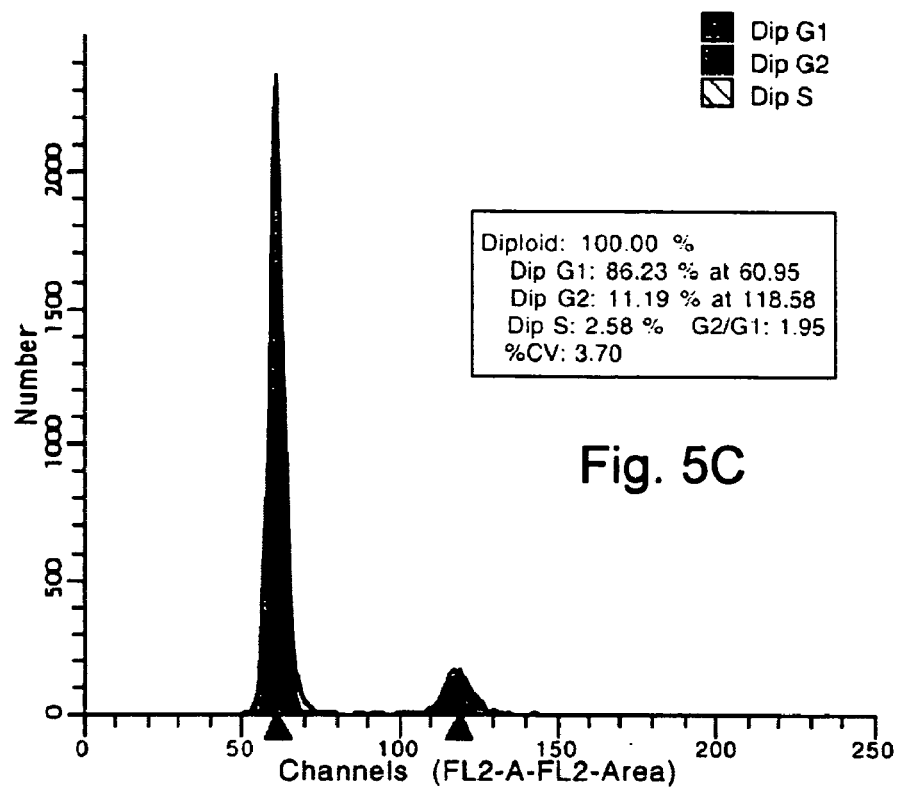
Figure 5D:
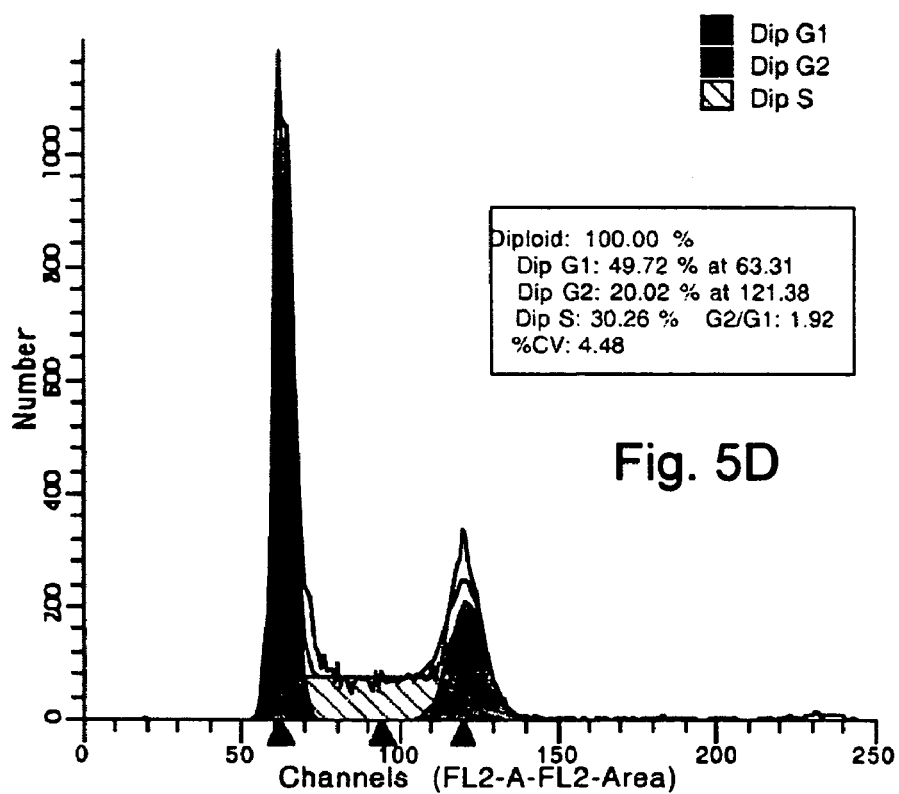
Figure 6A:
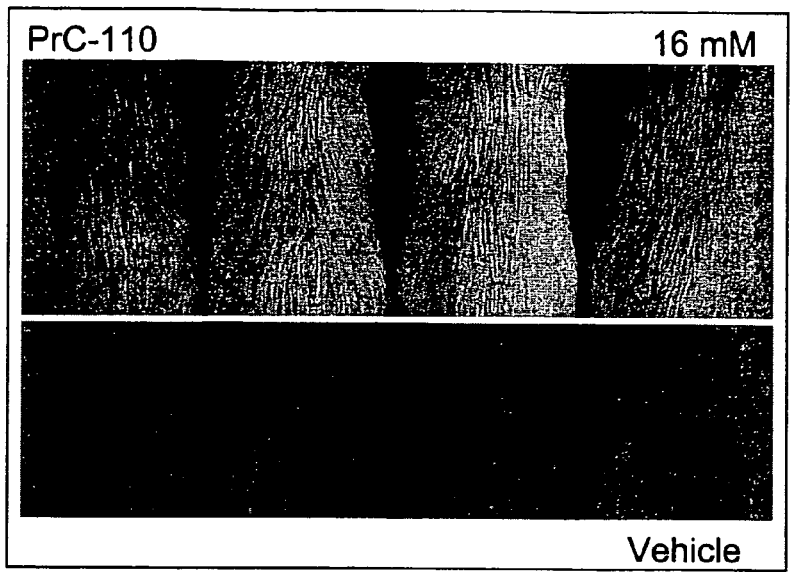
FIGS. 6A-6E illustrate the efficacy of topically-applied chemoprotective polyamines in protecting against chemotherapy-induced alopecia (hair loss) in a rodent model.
Figure 6B:
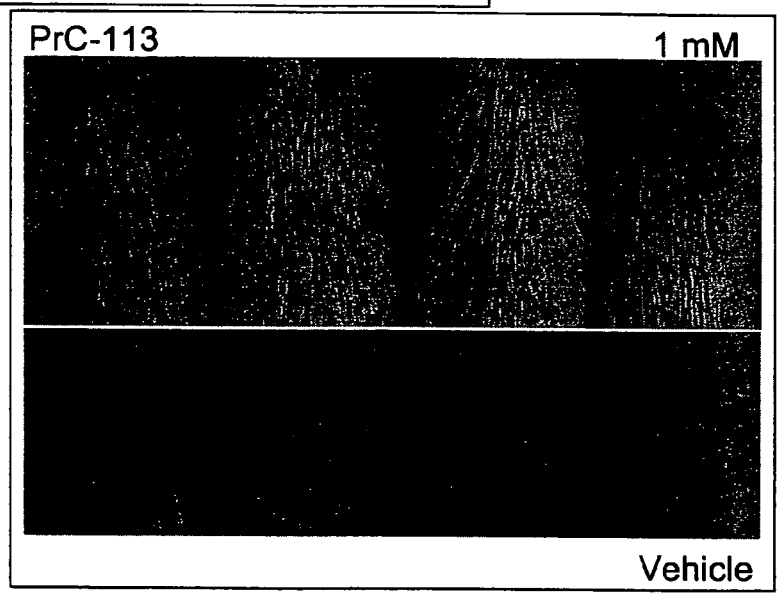
Figure 6C:
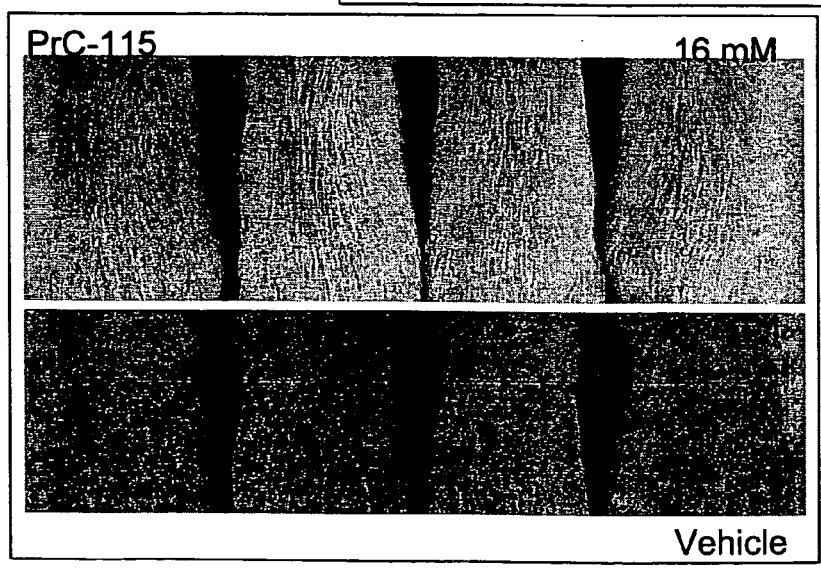
Figure 6D:
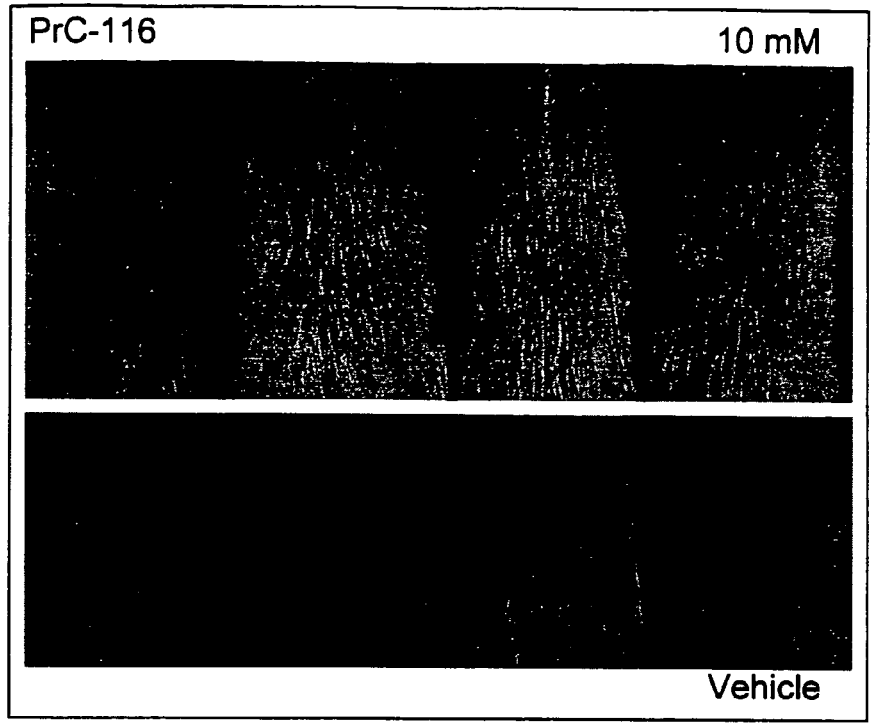
Figure 6E:
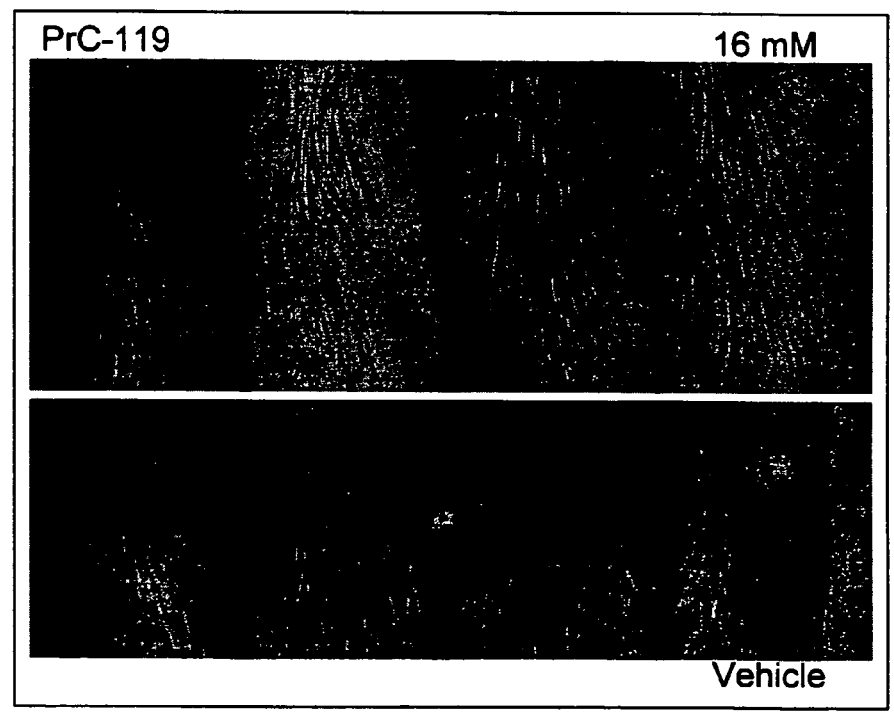

FIG. 3 illustrates that chemoprotective polyamines are able to induce expression of the negative cell cycle regulatory protein, p21, after exposing the human skin cells to the polyamine molecules. FIG. 3B shows that the induced p21 level is greater after a 30 hr exposure compared to a 50 hr exposure to drug. In these experiments, the 23SK human skin cells were exposed for 30 hr to an "$IC_{80}$" dose of each of the indicated chemoprotective polyamines and then lysed. Cell extracts were then prepared in order to measure p21 levels by western analysis (FIG. 3A). Results are summarized in Table 3. Although the ability of modified polyamines to induce p21 is known in the literature (Kramer, D. et al., Cancer Res. 59:1278-1286, 1999), it is a novel aspect of this invention that those chemoprotective polyamines with longer aliphatic "arms" were better able to induce expression of p21 as shown in FIG. 4.

TABLE 3

| Compound # | [MW:HCl salt] | p21 fold-induction at $IC_{80}$ Dose |
|---|---|---|
| PrC-110 | [523.9] | 2.91 |
| PrC-111 | [739.0] | 2.22 |
| PrC-112 | [954.2] | 2.45 |
| PrC-113 | [1169.3] | 3.21 |
| PrC-114 | [476.4] | — |
| PrC-115 | [691.6] | — |
| PrC-116 | [906.7] | 2.32 |
| PrC-117 | [1121.9] | ~3.0 |
| PrC-118 | [675.5] | — |
| PrC-119 | [725.0] | 1.80 |
| PrC-120 | [1155.3] | 2.01 |
| PrC-121 | [1169.3] | 3.26 |
| PrC-122 | [940.2] | 1.70 |
| PrC-123 | [906.7] | 2.22 |
| Colcemid | | 3.31 |

In FIG. 5, cell histograms showing the results from flow cytometry analysis of chemoprotective polyamine-treated 23SK skin cells are shown. FIG. 5A shows that for untreated, exponentially growing 23SK cells, 59.12% of the cells are present in the S+G2 cell cycle compartments, whereas only 40.88% of the cells are in the G1 compartment. FIG. 5B shows, as a control treatment, that incubation of cells in serum-free medium causes a sizable reduction in S+G2 cell compartments (down to 5.63% total), and a sizable increase in cells now present in the G1 compartment (up to 94.37%). FIG. 5C shows that cells treated with PrC-117 for 72 hr also show a marked reduction in S+G2 compartments (down to 13.77%) and a marked increase in the G1 compartment (up to 86.23%). FIG. 5D shows that after the cells treated with PrC-117 for 72 hr are switched for 48 hr to medium devoid of the Prc-117 molecule, the distribution within cell cycle compartments is basically returned to that seen in cells previously untreated with chemoprotective polyamine (i.e., FIG. 5A). The transient nature of the cell cycle block induced by chemoprotective polyamines is believed to be an important aspect of their efficacy, i.e., their ability to block cell cycle progression in stem cells during the course of chemo- or radiotherapy, and the resumption of normal stem cell division after a given cancer therapy course has been completed. Table 4 shows that, of the nine chemoprotective polyamine molecules tested, three caused G1 cell cycle blocks with greater than 75% of the cells present in the G1 compartment, and each of these three molecules contained 16 carbon aliphatic arms.

TABLE 4

| Compound # | [MW:HCl salt] | Cell Cycle Distribution At $IC_{80}$ Dose (%) | | |
|---|---|---|---|---|
| | | G1 | S | G2/M |
| PrC-110 | [523.9] | 60 | 26 | 14 |
| PrC-111 | [739.0] | 60 | 25 | 14 |
| PrC-112 | [954.2] | 61 | 23 | 16 |
| PrC-113 | [1169.3] | 77 | 8 | 14 |
| PrC-114 | [476.4] | — | | |
| PrC-115 | [691.6] | — | | |
| PrC-116 | [906.7] | 66 | 11 | 23 |
| PrC-117 | [1121.9] | 86 | 11 | 3 |
| PrC-118 | [675.5] | — | | |
| PrC-119 | [725.0] | — | | |
| PrC-120 | [1155.3] | — | | |
| PrC-121 | [1169.3] | 76 | 4 | 20 |
| PrC-122 | [940.2] | 67 | 15 | 18 |
| PrC-123 | [906.7] | 68 | 10 | 21 |
| Colcemid | | 8 | 11 | 81 |

Natural polyamines such as spermine, with a 3-4-3 configuration of aliphatic carbon chains containing terminal amine groups and separated by intervening amine groups, are known to bind avidly to cellular DNA in the cell setting. Synthetic polyamines, containing longer aliphatic carbon segments, typically of four carbons, have been shown to displace natural polyamines like spermine from DNA because of their greater binding affinity for helical DNA. At physiologic pH, each of the amine groups of a polyamine backbone can protonated to yield an ammonium cation. Therefore, as the length of a polyamine increases, achieved by oligomerizing a —$(CH_2)_4$—NH— segment, for example, there are typically an increased number of ammonium cations distributed along the polyamine backbone for bonding with anions distributed along the DNA backbone. As a result, longer, synthetic polyamine analogs compete more effectively with spermine in vitro and in vivo for binding to DNA. Binding of polyamines to helical DNA has also been shown to confer conformational changes to the DNA, such as conversion of helical B DNA to A or Z forms of DNA. And, in vivo, polyamine analogs have also been shown to cause condensation and aggregation of DNA and chromatin within mammalian cells (Basu, H., et al., Cancer Res. 49: 5591, 1989; Basu, H. et al., Biochem. J. 269:329, 1990). Though not intending to be bound by any particular theory, it is believed that his tight binding and associated distortion of normal helical structure, which is optimized in the design of chemoprotective polyamines of the present invention, provides pharmacologic benefit in at least three ways. First, the pharmacologic, growth inhibitory activity is reversible, as shown, for example, for the PrC-117 molecule in FIG. 5, i.e., by simply stopping topical application, the treated cells are released from growth inhibition thus yielding a 'transient' growth regulation. Second, distortion of helical DNA and the formation of single-stranded bubbles is likely to be the cause, or to be closely related to the cause, of the induced expression of p21 and the G1 cell cycle block that is associated with its induced expression. Third, for many electrophilic, alkylating drugs, reaction with DNA occurs in two steps, the first step requiring intercalation of the drug molecule between nucleoside bases in helical B DNA, and a rapid second step involving alkylation of the adjacent DNA base by the drug molecule. By condensing and altering normal DNA helical form, chemoprotective polyamines are expected to significantly reduce alkylation of cellular DNA by electrophilic drugs. Likewise, condensation and alteration of DNA helical form by polyamine binding in vitro has also been shown to dramatically reduce the number of single strand breaks induced when the DNA is directly irradiated in vitro (Spotheim, M., Int. J. Radiat. Biol. 68: 571-577, 1995).

When comparing chemoprotective polyamines to those polyamine analogs that have been previously described, there are a number of marked differences. For instance, Edwards (U.S. Pat. Nos. 5,217,964 and 5,434,145) attached one or more alkyl-thiophosphate or alkyl-thiol groups to one or more of the backbone amines of short aliphatic polyamines, or to one or more backbone amines as well as to one or more terminal benzyl groups on equally short polyamines. In comparison, the present inventors have designed and synthesized chemoprotective polyamine molecules which: i) optimize both the polyamine side chain ("arm") length and overall molecule length to achieve tight DNA binding, ii) project or "display" a protective functional group physically away from the DNA to which the chemoprotective polyamine is strongly bound, iii) attach the functional group to a polyamine backbone carbon atom instead of to one of the backbone amine groups, iv) in certain embodiments, display functional groups from allylic positions of olefinic core segments that are present in chemoprotective polyamines; this is done by design to enhance reactivity of the group, v) include a range of functional groups that are "displayed," including —SH, —OH, —$NH_2$, —NHR, —$NR_2$, —SH and —$SCH_3$ moieties, singly or in combination, as well as other groups that are known to vary in their degree of nucleophilicity or ability to scavenge free radicals, vi) include the display of more than one functional group per polyamine molecule, and vii) in some embodiments, include a rigid platform from which the functional group is projected or displayed on a spacer aliphatic chain away from the DNA in a manner that better enables the "sentinel group" to scavenge or trap electrophiles/oxygen radicals from the cellular milieu before they attack other known nucleophilic groups within DNA, such as the 2-amino group of deoxyguanosine.

This ability to scavenge and trap chemical/physical reactants within a cell does not require the chemoprotective polyamine to be physically attached to cellular DNA or RNA. Rather, simple molar presence of such nucleophilic or other protective functional groups in cells would be expected to be protective. For instance, previous work in the field has shown a positive, linear correlation between the intracellular concentration of the physiologic nucleophile, glutathione (GSH), and the concentration of an electrophile required to kill the exposed cells (Ho, D. and Fahl, W. E., J. Biol. Chem. 259: 11231-11235, 1984). In another mechanism by which chemoprotective polyamines might protect cells against cytotoxic threats, they may serve as a "stealth" vehicle by which to load cells with —SH or other nucleophilic or protective groups. Whereas, it is well known in the field (Levy, E. et al., Proc. Natl. Acad. Sci. USA 90:9171-9175, 1993) that the SH-containing nucleophile, glutathione, is not taken up by cells in a physiologic setting, the cell membrane polyamine transporter (PTS), which is known to mediate the uptake of polyamines, molecules containing multiple charged sites, should efficiently transport functional group-displaying polyamines into cells, and that this would provide an efficient means to "load" cells with, e.g., an SH-containing polyamine, which could serve as a glutathione surrogate. Once loaded with the polyamine, these cells would be protected from subsequent toxic challenges, such as those seen with transient chemotherapy and radiotherapy regimens. The results in the tables and figures that show the same growth regulating efficacy for each of the SH-containing chemoprotective polyamines (i.e., PrC-114, PrC-115, PrC-116, PrC-117) as for those chemoprotective polyamines without SH groups implies that the SH-containing molecules are transported into the human fibroblasts equally well, and that they bind with equal affinity to cellular DNA. Moreover, the fact that each of the SH-displaying chemoprotective polyamines exemplified herein has shown protective activity in the rat cytoxan-induced alopecia assay demonstrates that the displayed nucleophile is also active within the cell milieu.

Another way to increase the molar presence of nucleophiles/scavengers within the nuclear environs is to display more than one such functional group on each chemoprotective polyamine molecule. In embodiments where two —SH groups are displayed on a single polyamine, then a reducing agent such as sodium borohydride or others as known in the art may added to the pharmaceutical preparation to reduce any —S—S— disulfide bonds that might be formed when —SH groups are present in an oxygen containing medium. An alternate strategy to avoid disulfide bond formation is to "cap" the displayed sulfur atom with a $CH_3$ group to prevent interaction of the sulfur atoms, while still retaining the capacity of the sulfur atom to scavenge electrophiles/oxygen radicals.

The use and placement of protective functional groups on the backbone of chemoprotective polyamines is also significantly different from the attachment of —$CH_2CH_2SPO_3H_2$ or —$CH_2CH_2SH$ groups to polyamines described by Edwards in U.S. Pat. Nos. 5,434,145 and 5,217,964. In U.S. Pat. No. 5,434,145, Edwards showed bonding of alkyl-thiophosphate or alkyl-thiol groups to one or more of the 3-4 backbone amines present in the short polyamine molecules. By modifying the secondary amines in the polyamine backbone with alkyl-thiophosphate groups, the amines were converted to tertiary amines, which markedly alters the basicity of the individual modified amine, as well as the overall polyamine molecule. The attenuated basicity of the individual amine groups is accompanied by an alteration in 3-dimensional structure at these sites. With added alkyl functionality on the amine nitrogen atoms, steric bulkiness increases, so the ability or freedom of the molecule to rotate and twist at these sites is markedly reduced. The altered basicity and steric constraints in these short spermine-like polyamines perturbs DNA binding by the polyamine as compared to their natural polyamine counterparts. Given the already very high $IC_{50}$ concentration of spermine for DNA binding/precipitation (nearly 1,000-fold higher than for most chemoprotective polyamines; see Table 2), it is possible that the modification of backbone amines described by Edwards would eliminate DNA binding altogether in cells at the concentrations of drug that could be pharmacologically achieved. The attenuated basicity of the amine-modified polyamine molecules in Edwards could also affect their pharmacologic delivery characteristics. In topical applications to skin and other epithelial surfaces, there is an accepted relationship between the degree of ionization at physiologic pH of an applied drug and the degree to which it permeates or traverses the surface cells. In contrast to Edwards, the functional group used in the chemoprotective polyamines of the invention, whether —SH or one of several other groups (e.g., OH, N-ethyl, N-methyl, N-dimethyl; see FIG. 1), is bound to a carbon atom within the polyamine backbone. This was done specifically to avoid perturbing the DNA binding characteristics of each of the backbone amine groups, while still achieving the display of reactive functional groups.

In U.S. Pat. No. 5,217,964, Edwards discloses the linking of one or more alkyl-thiophosphate or alkyl-thiol groups to the polyamine backbone through one or more terminal benzyl group(s) or through one or more of the backbone amine groups. Work within the field (Huber, M., J. Biol. Chem. 271:27556-27563, 1996) has shown that polyamines containing one or more aromatic groups are well-suited to serve as inhibitors of the membrane polyamine uptake transporter, and predictably, they themselves are not taken up into cells. Consistent with the above observations, Edwards provides no information regarding biological activity for any of the structures proposed in U.S. Pat. No. 5,217,964 or U.S. Pat. No. 5,434,145.

FIGS. 6A-6E illustrate the efficacy of each of the indicated chemoprotective polyamines in protecting against Cytoxan-induced alopecia in the rat model (Hussein et al., 1990, infra). In this protocol (See Example 2), chemoprotective polyamines are applied topically to the rat pups' backs in an alcohol:water delivery vehicle, once per day, for five days before and five days after a single systemic dose of Cytoxan. As seen, topical chemoprotective polyamines conferred significant protection against the generalized alopecia that was seen to occur in the vehicle-treated rat pups.

3. Topical or Local Administration of Pharmaceutical Preparations

As described above, the chemoprotective polyamines of the present invention have been shown to inhibit the growth of normal human skin cells, to modify normal B-DNA helical structure, to induce expression of the negative cell cycle regulator, p21, to cause a G1-specific cell cycle block, and to protect against chemotherapy-induced alopecia and dermatitis in an animal model. Thus, the compounds of the invention are particularly suitable for treatment of humans to prevent the local side effects of cancer chemotherapy and radiotherapy. Based upon their growth regulatory effects, chemoprotective polyamines may also find utility in other applications where inhibition of cell growth would be advantageous, including regulating proliferative conditions of the skin, such as psoriasis and dermal nevus.

Two important targets for delivery of such protective therapies are (1) the epithelial cells of the skin, including hair follicles and the epidermis, and (2) the epithelial cells lining the oral and entire gastrointestinal (GI) or urogenital tract. The method of protection of these tissues with chemoprotective polyamine comprises administering to a population of epithelial cells a composition consisting of a chemoprotective polyamine and a delivery vehicle for a time and in an amount effective to protect the non-neoplastic cells from damage during the cancer chemotherapy or radiotherapy. In one embodiment, the method is used to prevent alopecia during cancer therapy, by topically applying the composition to the scalp. In another embodiment, the method is used to prevent gastrointestinal distress due to cancer therapy by administering the composition orally. In another embodiment, the method is used to prevent mucositis from chemotherapy or radiotherapy by administering the composition topically to the appropriate region of the body. In yet another embodiment, the method is used to prevent radiation-induced dermatitis, skin rash, and ulceration at the site of irradiation by applying the composition to the skin.

Administration of chemoprotective polyamines to human or non-human subjects can be achieved in several ways. The preferred administration route is topical, to tissue sites including the skin, as well as oropharyngeal and gastrointestinal mucosal surfaces. It can also be delivered locally to an internal organ, tissue or regions thereof. It should be noted, as with all pharmaceuticals, the concentration and total amount of polyamine administered will vary depending upon the tissue being treated, the mode of administration, the size and condition of the subject being treated, and the particular chemoprotective polyamine being used.

Compositions of chemoprotective polyamines formulated in delivery vehicles are well-suited to be administered topically to the skin or surfaces of the mouth, GI or urogenital tract. Pharmacologic concentrations of chemoprotective polyamines can protect normal, non-neoplastic cells from cancer therapy-associated cell damage. By producing a local gradient effect within the tissues, the topically applied polyamine produces a local protective effect at the intended region. This dose-dependant gradient of topical drug can effectively protect normal proliferating cells rendering them less susceptible to radiation or chemotherapy. Importantly, while this local effect would protect normal cells, in contrast, any deeper-seated tumor cells would be less affected by the topical polyamine composition, and would remain sensitive to the cancer therapeutic. Moreover, topical delivery of a chemoprotective polyamine, which has a highly positive charge at physiologic pH, should diminish any systemic exposure and limit the effect on any tumor cells or normal host organ cells. Given the host toxicity that has been previously observed when polyamine analogs were administered systemically (Creaven, P. et al., Invest. New Drugs 15:227-234, 1997; Streiff, Rand Bender, J., Invest. New Drugs 19:29-39, 2001), this provides another important reason to avoid systemic delivery of the chemoprotective polyamine molecules. The intended protection of normal tissue is achieved by an appropriate formulation of chemoprotective polyamine in combination with an appropriate delivery vehicle depending on the administration site (e.g. dermal/intradermal or mucosal). A pharmaceutical composition comprising a chemoprotective polyamine formulated with an appropriate delivery vehicle will have utility in any normal cell type susceptible to the side effects of cancer therapy that is accessible by topical delivery.

Thus, the chemoprotective polyamines of the invention are administered topically (or locally) to protect patients from the side effects of cancer therapy. The term "topical" denotes the administration of a drug intended to act locally rather than systemically. In the present invention, "topical" or "local" delivery is directed to epidermal and dermal cells of the skin and scalp (including cells lining hair follicles), as well as mucosal cells of the mouth, salivary glands, throat, gastrointestinal system and urogenital tract. For some of these latter locations, compositions may be formulated for oral or nasal delivery, or as suppositories. The goal of such delivery systems is to contact these internal surfaces topically with the polyamine effectors.

The local delivery of drug molecules within the skin or mucous membranes using a noninvasive delivery system has many attractions, including patient acceptability due to the noninvasiveness of the procedure, avoidance of gastrointestinal digestion and disturbances, and first-pass metabolism of the delivered molecule. Topical delivery is not an efficient means for systemic drug delivery. It is estimated that only between 1%-15% of a drug in most topical formulations is systemically bioavailable. In preferred embodiments of the invention, less than 10%, preferably less than 5% and most preferably less than 1% of the polyamine effector, provided topically e.g., dermal, intradermal, mucosal or GI epithelial delivery, move to reach the dermis and/or other underlying tissues.

Topical delivery vehicles can take the form of aqueous or aqueous:alcohol solutions, emulsions, creams, lotions, ointments, gels or liposomes.

Solutions are the most traditional types of formulations for topical dermal drugs, where the agent is solubilized in a solvent. Solvent-based systems are simple and effective constituents of topical delivery vehicles for some drugs. Alcohols are the most commonly used solvents for topical solutions. Typically, the drug is combined into a water and alcohol mixture. The alcohol content varies between 10-100%. Alcohols used include ethanol, propylene glycol, polyethylene glycols, methanol, or butanediol. Each of these types of alcohols is suitable for use in the present invention; others not listed are also suitable, as would be understood by one of skill in the art. High alcohol content solutions such as solutions of 70% ethanol in water or ones containing 60% ethanol, 20% propylene glycol and 20% water, are particularly good at penetrating the stratum corneum of the epidermis. Topical minoxidil, a hair regrowth treatment, uses the latter formulation as the delivery vehicle.

Solution-based delivery systems are particularly suitable for the delivery of small organic molecules. In a preferred embodiment of the invention, particularly for administration of chemoprotective polyamines to the epidermis, alcoholic solutions, as described above, are utilized. An aqueous alcohol-based delivery vehicle has been proven to be highly effective for topical administration of chemoprotective polyamines. Advantages of this delivery system include, ease of manufacturing, ease of application, fast drying, lack of residue on skin, and ease of analysis of active drug compound after formulation. Solution-type formulations are typically administered using dropper bottles or as aerosols.

Emulsions form the basis of cream and lotion-type formulations. Typically, these formulations are colloidal dispersions composed of two immiscible phases; an oil phase and an aqueous phase with an emulsifier. Typical oils used in emulsions include stearyl alcohol, isopropyl lanolate, isopropyl myristate, cetyl alcohol, and vitamin E. Emulsifiers are essentially surfactants that lower the surface tension of the immiscible phases. Most emulsifiers tend to be fatty acid esters or stearates of glycerol, sorbitan, or polyoxyethylene (POE). Depending on the location of the oil and water, emulsions are oil-in-water, water-in-oil or combinations thereof. The preparation of an emulsion commonly requires some mechanical shear force with heat to mix the internal and external phases. Most topical emulsions contain viscosity builders such as natural gums (alginates, carrageenan, tragacanth, pectin, xanthan or collagen) at 1-5% to thicken the preparation. Higher percentages of viscosity builders produce creams, a lower percentage form lotions. Complete formulations for emulsions (creams and lotions) generally include water, alcohol, propylene glycol, sodium lauryl sulfate and white wax. In alternative formulations, they include water, alcohol, glycerol, phosphatidyl choline, lysophosphatidyl choline and triglycerides. For administration of chemoprotective polyamines to the epidermis, emulsions are particularly well suited. Ease of administration, good local retention and slow release of drug are some of the attractive characteristics of emulsions for a topical delivery system.

Ointments are composed of fluid hydrocarbons meshed in a matrix of higher melting solid hydrocarbons. The hydrocarbon ointment base is typically petrolatum and white ointment. Ointments are prepared by melting the base, followed by the addition of excipients, such as antioxidants to the fluid. The drug is then suspended into the ointment by milling. Due to the high oil content, ointments tend to be greasy. Adding components, such as microcrystalline cellulose, which gives the ointment a dry feel on the skin, can reduce greasiness. All ingredients listed above for preparation of ointments are suitable for use in the present invention, as well as unlisted ingredients typically employed for such purpose by one of skill in the art.

Gels are semisolids consisting of a gelling agent that is penetrated with liquid solvent. The concentration and the molecular weight of the gelling agent affect the consistency of vehicle formulation. The gelling agent is a suspension of either large organic or small inorganic molecules. The large organic molecules consisting of either natural or synthetic polymers exist as randomly coiled chains that entangle and form the gel structure. Some common polymers of this kind are natural gums, cellulose derivatives and acrylic acid polymers. Another class of these gels, called thermally sensitive gels, is prepared from poloxamers. In contrast, the small inorganic molecules form the gel structure by forming a somewhat organized three-dimensional network. Common small inorganic polymers include colloidal solids found in silica and clays. The nature of the solvent determines whether the gel is a hydrogel (water-based) or an organogel (non-aqueous solvent based). Gels are attractive topical delivery vehicles for chemoprotective polyamines because they are relatively easy to prepare and tend to have a long residence time at the site of application allowing the slow release of compound at the desired site. All ingredients listed above for preparation of gels are suitable for use in the present invention, as well as unlisted ingredients typically employed by one skilled in the art for such purpose.

Liposomes are vesicles consisting of amphipathic lipids arranged in one or more concentric bilayers. When lipids are placed in aqueous medium, the hydrophilic interaction of the lipid head groups with water results in the formation of multilamellar and unilamellar systems or vesicles which resemble biological membranes in the form of a spherical shell. Liposomes may be small (0.025-0.05 um) to large multilamellar vesicles (0.05-10 um). Lipids used to prepare the liposomes include phospholipids, sphingolipids, glycosphingolipids, saturated glycerides, steroids (e.g., cholesterol) and synthetic phospholipids. Liposomes are typically prepared by melting the lipid together in aqueous solvent with an emulsifier like POE. The drug is then added and the liposomes are generated through mixing or sonication. The drug is usually entrapped in the vesicle structure. These basic liposomes are sometimes referred to as "conventional liposomes." Several other types of liposomal preparations exist, including (1) sterically stabilized liposomes, which are surface coated with an inert hydrophilic polymer, such as polyethylene glycol; (2) targeted liposomes, to which are attached targeting ligands, such as antibodies or fragments thereof, lectins, oligosaccharides or peptides (e.g., choleratoxin B (CTB) is used to target liposomes to the gastrointestinal epithelium); and (3) reactive or "polymorphic" liposomes, which change their phase and structure in response to a particular interaction (this group includes liposomes sensitive to ions (pH, cations), heat and light, among other stimuli.

Liposomes are good vehicles for dermatological applications. Liposomal delivery offers certain advantages over more conventional formulations, including: (1) reduced serious side effects and incompatability from undesirably high systemic absorption; (2) significantly enhanced accumulation of the delivered substance at the site of administration due to high compatability of liposomes with stratum corneum; (3) ready incorporation of a wide variety of hydrophilic and hydrophobic molecules into the skin; (4) protection of the entrapped compound from metabolic degradation; and (5) close resemblance to the natural membrane structure and their associated biocompatibility and biodegradability. All ingredients listed above and for preparation of various types of liposomes are suitable for use in the present invention, as well as any other such ingredients typically employed by one skilled in the art for such purpose.

In order to achieve efficient delivery of a chemoprotective polyamine into the skin, one embodiment of the invention includes various formulations of liposomes (phospholipid-based vesicles, cationic liposomes, nonionic liposomes, non ionic/cationic liposomes, pegylated liposomes, PINC polymer, and propylene glycol and ethanol mixture (commonly used vehicle for administering minoxidil), and nonionic liposome/propylene glycol and ethanol mixtures. Reactive liposomes may be preferred for other embodiments of the present invention. Inclusion of cationic amphiphiles as aminor component of liposomes facilitates the association with negatively charged solutes, the rapid binding of liposomes to the cell surface, and the cellular uptake of liposomes. pH-sensitive liposomes have been developed to improve the efficiency of the cytoplasmic delivery of antitumor drugs, proteins, and nucleic acids. Most pH-sensitive liposomes have been prepared using phosphatidylethanolamine (PE). PE alone does not form liposomes and is prone to form the inverted hexagonal phase (HII). However, liposomes can be prepared by adding another bilayer-stabilizing, amphiphilic lipid component to PE. Titratable amphiphiles having a carboxyl group have been used as a component for the preparation of pH-sensitive liposomes. Because the ability to stabilize a bilayer membrane by these titratable amphiphiles decreases under acidic conditions, destabilization results in the fusion of the liposomes. pH-sensitive liposomes are stable at physiological pH, and are internalized by cells through an endocytic pathway, which exposes the liposomes to an acidic pH. Liposomes within the endosome are destabilized and possibly fuse with the endosome membrane, resulting in release of their contents into the cytoplasm without degradation by lysosomal enzymes.

In other embodiments of the invention, sterically stabilized, inert liposomes are particularly suitable. In still other embodiments, targeted liposomes may be used to advantage.

For many applications, mucosal delivery will be used for delivery of chemoprotective polyamines. Mucosal delivery defined here is the local delivery of polyamine effectors to the mucosa of the mouth, GI, and urogenital tract. Mucosally active drugs, can be formulated as either solutions, emulsions or creams, ointments, gels or liposomes using the ingredients described above. In addition, there are also special excipients specifically designed for mucosal delivery. The description, composition, and applicability of these major types of mucosal delivery forms are set forth below. Each is considered suitable for practice of various embodiments of the present invention.

In general, the structure of the mucosal surface is composed of an outermost layer of stratified squamous epithelium, below which lie a basement membrane, a lamina propria followed by the submucosa as the inner-most layer. The mucosae of areas subject to mechanical stress such as the gingivae or the hard palate are also keratinized, similar to the epidermis. Depending on the keratinization, the mucosa is somewhat permeable. The permeability of oral mucosa is 4-4000 times greater than that of the skin. Permeability of intestinal mucosa is even greater. The cells of the epithelia are surrounded by an intercellular ground substance, mucous, the principal components of which are complexes of proteins, carbohydrates, lipids and ceramides. Primarily, special mucous-secreting cells, called goblet cells, synthesize mucous. However, in the oral mucosa, most of the mucous is produced by the major and minor salivary glands. Mucous forms a strongly cohesive gel structure that will bind to the epithelial cell surface as a gelatinous layer. The penetration of this mucous layer and the local retention of compound because of its permeability must be achieved for effective mucosal drug delivery. However, this route of administration is very important for the delivery of compounds designed to protect mucosal surfaces from cancer therapy. Since the mucosal surface is a common site in which many of the unwanted side effects occur, the use of formulated mucosally-active drugs designed to prevent these effects is warranted.

Issues to be considered with mucosal delivery are (1) low flux or drug transport through the mucous layer and (2) poor retention and bioadhesion at the mucosal site. Mucosal permeation enhancers are designed to improve drug flux or penetration at the mucosal surface. The use of these enhancers can increase drug permeability by 100-fold or more. Various permeation/absorption enhancers vary in molecular weight and physicochemical properties. In a preferred embodiment for mucosal delivery, permeation enhancers are included in formulations for delivery of chemoprotective polyamines to the mucosal surface. Most types of enhancers are detergents that include: sodium glycocholate, sodium taurocholate, polysorbate 80, sodium lauryl sulfate, lauric acid, and various alkyl glycosides. Other examples of enhancers include: dextrins (cyclodextrin, dextran sulfate), fatty acids (phosphatidylcholine, lysophosphatidylcholine), heterocyclic compounds (azone), and small molecules (benzalkonium chloride, cetyltrimethylammonium bromide). Each is contemplated for use in the present invention as are other unlisted ingredients typically used for such purpose, as would be appreciated by one of skill in the art.

The addition of mucoadhesives to the formulation can improve local retention of mucosally delivered compounds. In another preferred embodiment for mucosal delivery, mucoadhesives are included in the polyamine effector formulations of the invention. Mucoadhesive compounds are primarily synthetic or natural polymers that can adhere to the wet mucosal surface. These include synthetic polymers such as monomeric alpha cyanoacrylate, polyacrylic acid, hydroxypropyl methylcellulose, and poly methacrylate derivatives. Glue-like polymers include epoxy resins and polyurethanes. Naturally occurring mucoadhesives include chitosan, hyaluronic acid and xanthan gum. Each is contemplated for use in the present invention as are other unlisted ingredients typically used for such purpose, as would be appreciated by one of skill in the art.

Other delivery vehicles are also suitable for use in the present invention, particularly for administration of polyamine effectors to the mucosa and lumen of the GI and urogenital tract. Nonlimiting examples include: (1) oils such as vegetable oils or fish oils (which can be encapsulated into standard gel capsules); and (2) emulsions prepared, for example, by dispersing polyoxyethylene ethers, e.g., 10-stearyl ether (Brij 76) in aqueous buffer.

Other examples of delivery vehicles suitable for the GI or urogenital mucosa include biodegradable microparticles (preferably in the range of 0.1-10 uM diameter) of polylactic polyglycolic acid, which have been used to deliver proteins to Caco-2 cells as an in vitro model system for gastrointestinal uptake via oral drug delivery (Desai et al., Pharm. Res. 14: 1568-1573, 1997). Significant uptake of proteins carried by polystyrene particles into cells lining the small intestine of the rat has been demonstrated (Hillery et al., J. Drug Targeting 2: 151-156, 1994). Indeed, delivery of protein-containing microparticles has been reported from the GI lumen all the way to the submucosal vasculature (Aphramaian et al., Biol. Cell 61: 69-76, 1987). Therefore, such polymeric microparticles are quite suitable for oral delivery of polyamine effectors to gastrointestinal epithelial cells, which are found on the surface of the GI lumen.

Thus, chemoprotective polyamines are formulated as pharmaceutical preparations for topical or local administration to patients. The following sites of local administration of these pharmaceutical preparations are contemplated: oral, nasal, ophthalmic, gastrointestinal, urogenital and dermal (cutaneous). The term "patient" or "subject" as used herein refers to human or animal subjects (animals being particularly useful as models for clinical efficacy of a particular composition). Selection of a suitable pharmaceutical preparation depends upon the method of administration chosen, and may be made according to protocols well known to medicinal chemists.

The pharmaceutical preparation comprising the compositions of the invention are conveniently formulated for administration with a biologically acceptable medium such as water, buffered saline, alcohols, polyol (for example, glycerol, propylene glycol, liquid polyethylene glycol and the like), dimethyl sulfoxide (DMSO), oils, detergents, suspending agents or suitable mixtures thereof, as compatible with the specific delivery vehicles described above. The concentration of a particular composition in the chosen medium will depend on the hydrophobic or hydrophilic nature of the medium, in combination with the specific properties of the delivery vehicle and active agents disposed therein. As used herein, "biologically acceptable" or "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

The topical formulation can contain a variety of excipients that function to stabilize and solubilize the drug formulation, increase permeation, and protect and aid in the application to the skin. Oil or water-based excipients are primarily added to improve drug solubility and spreadibility to the formulation. Surfactants may be added to topical formulations as detergents, solubilizers, emulsifiers, and wetting agents.

It will also be appreciated by persons of skill in the art that pharmaceutical formulations of the invention may contain more than one chemoprotective polyamine. Various combinations of such agents may be useful for certain applications, and formulations of such combinations would be prepared according to the general guidelines set forth above. Moreover, one or more chemoprotective polyamines may be combined with other agents, such as other anti-proliferative agents or chemoprotective drugs, to provide a pharmaceutical formulation that is effective by two different modes of action. An anti-proliferative agent suitable for such use is the cyclin-dependent kinase II inhibitor described in PCT application US00/05186, published Dec. 28, 2000 as WO 00/78289 or genistein, an inhibitor of tyrosine protein kinase. A chemoprotective agent suitable for such use is resveratrol (trihydroxy-trans-stilbene). Several classes of "chemoprotective inducing agents" (agents that induce the cell's endogenous defense processes) that may be combined with the chemoprotective polyamines of the invention are described in detail in commonly-owned, co-pending U.S. application Ser. No. 09/565,714, filed May 5, 2000, and International Application No. PCT US01/14464, filed May 4, 2001, the entireties of each of which are incorporated by reference herein. Further, certain of those chemoprotective inducing agents also possess anti-proliferative activity.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of the chemoprotective polyamine calculated to produce the desired protective effect in association with the selected pharmaceutical carrier. Procedures for determining the appropriate dosage unit are well known to those skilled in the art. As used herein, "therapeutically effective amount" refers to an amount of a compound as described herein that may be effective to inhibit, or treat the symptoms of particular disorder or side effect. The term "prophylactically effective amount" refers to an amount of a compound as described herein that may be effective to prevent, inhibit, or diminish the onset the symptoms of a particular disorder or side effect.

Dosage units may be proportionately increased or decreased based on the height and weight of the patient. Appropriate concentrations for achieving protection of a target cell population or tissue from the toxic effect of a particular chemotherapeutic agent may be determined by dosage concentration curve calculations, as known in the art.

As one example, for topical applications, the chemoprotective polyamine may be used at concentrations ranging from 1-100 mM in an appropriate carrier (e.g., alcohol solvent) applied to the scalp or other dermal site. This dosage is arrived at from results of experiments using a rodent model and the range of dosages is a function of results obtained from experiments using several different molecules that ranged in dose effectiveness. The volume of material applied to the skin ranges by size of surface area to be covered; e.g., scalp treatment for young children requiring 3-5 ml, the amount being increased in adults to 10-20 ml per application.

As another example, for gastrointestinal administration, the oral dose of the chemoprotective polyamine in an appropriate medium (e.g., solvent, liposome emulsion) is normalized to the lumenal surface area of the stomach and duodenum. This would assume that the patient consumes the material on an empty stomach upon rising in the morning.

The pharmaceutical preparation comprising the compositions of the invention may be administered at appropriate intervals, before, during, or after a regimen of chemotherapy and/or radiotherapy. The appropriate interval in a particular case would normally depend on the nature of the chemotherapy or radiotherapy and the cell population targeted for protection.

For instance, for prevention of chemotherapy-induced alopecia, solvents, liposomes or other delivery vehicles containing the chemoprotective polyamine can be further formulated to be delivered, (e.g., as a topical cream, or gel) to the scalp of a patient prior to scheduled administration of chemotherapy. By protecting the epithelial cells that line the exposed surface of hair follicles from the chemotherapy drug, the loss of hair commonly associated with cancer chemotherapy is prevented. Likewise, for the treatment of radiation-induced dermatitis, the chemoprotective polyamine can be further formulated as a gel, ointment or cream containing moisturizers. This would further protect the epidermis from radiation damage. The topical formulation preferably is initiated several days prior to the cancer therapy, to ensure that the epithelial and mucosal cells are adequately treated. The formulation may then continue to be applied during the course of chemotherapy.

For protection of the gastrointestinal epithelium, the chemoprotective polyamine is formulated to be delivered by mouth to a patient prior to scheduled administration of cancer therapy. Administration of the protective formulation in the 1-5 days prior to radiotherapy or the infusion of the chemotherapeutic agent thus confers protection to susceptible mucosal epithelial cells. For example, the patient would be instructed to consume a "shake" containing the chemoprotective polyamine in an orally acceptable solution or liposome emulsion before breakfast in the morning, in the 1-5 days preceding chemotherapy. This would allow the chemoprotective polyamine to be present when the chemotherapy drugs or radiotherapy act on the GI mucosal epithelium.

The examples that follow are included to aid in a more complete understanding of the present invention. The examples do not limit the invention disclosed and claimed herein in any fashion. Reference numerals are to the reaction schemes described above. All purification columns were carried out using silica gel (230-400 mesh) with eluant noted. Silica gel plates (250 micron) were used for all thin layer chromatography (TLC) with the appropriate solvent system noted.

EXAMPLE 1

Preparation of Compounds Used in Synthetic Schemes

Scheme 1:

Compound 2:2 M ethylamine (compound 1) in tetrahydrofuran was stirred in a pressure bottle at <0° C. and mesitylene sulfonyl chloride (3 molar equivalents wrt ethylamine) was added in portions so that the temperature did not exceed 10°

C. Dichloromethane and triethylamine were added and the pressure bottle sealed. The reaction was stirred in a 30° C. water bath for one hour and at RT for 30 minutes. The reaction progress was monitored by TLC using 8:2 heptanes:ethyl acetate as the mobile phase. Water was added and the organic layer was separated, the water layer was extracted once with dichloromethane, the combined organic layers were washed twice with water and condensed under vacuum. The product was used without further purification.

Compound 3: NaH (1.2 molar equivalents wrt compound A) was stirred, under $N_2$, at 10° C. and dimethylformamide was added. Compound 2 dissolved in tetrahydrofuran was added and stirred until the evolution of $H_2$ gas ceased. Bromobutyl (or any N-alkyl depending on desired distance between amines)-phthalimide (1.1 molar equivalents wrt to compound 2) was added in one portion and NaI was added. The reaction was heated to 60° C. and the progress monitored after several hours by TLC using 7:3 heptanes: ethyl acetate as the mobile phase. The reaction contents were condensed under vacuum and dissolved in ethyl acetate and water. The organic layer was separated, the aqueous layer was extracted with ethyl acetate, and the combined organic layers were washed with dilute brine and condensed under vacuum. The product was used without further purification.

Compound 4: Ethanol was heated to 70° C. and compound B dissolved in hot ethanol was added. Hydrazine hydrate (2.5 molar equivalents wrt compound 3) was added all at once and the reaction was stirred at 70° C. overnight. The reaction progress was monitored by TLC using 6:4 heptanes:ethyl acetate as the mobile phase. The completed reaction was cooled on ice and a white precipitate formed. The precipitate was removed by filtration and the filtrate condensed under vacuum. The resulting semisolid was dissolved in dichloromethane and water. The organic layer was separated, the aqueous layer was extracted with dichloromethane and the combined organic layers were washed with water and condensed under vacuum. The product was purified by column chromatography using silica gel and 90:9:1 dichloromethane: methanol: ammonium hydroxide as the eluant.

Compound 5: Mesitylene sulfonyl chloride (1.1 molar equivalents wrt compound 4) dissolved in dichloromethane was stirred, under $N_2$, at 10° C. Compound C dissolved in dichloromethane was slowly added so that the temperature did not exceed 15° C. The reaction was cooled to 10° C. and triethylamine (1.2 molar equivalents wrt compound 4) was added. The reaction was stirred at RT for several hours. The progress was monitored by TLC using 1:1 heptanes:ethyl acetate as the mobile phase. The reaction was quenched by adding water and stirring for 20 minutes. The organic layer was separated, the aqueous layer was extracted with ethyl acetate then dichloromethane, and the combined organic layers were washed with water and condensed under vacuum. The product was purified by column chromatography using silica gel and 6:4 heptanes:ethyl acetate as the eluant.

The polyamine side chains are elongated by repeating steps 2-4 until the desired length is reached.

Scheme 2:

Compound 16: Dihydroxyacetone dimer, compound 15, was stirred in dimethylformamide, under $N_2$, at 2° C. Imidazole (5.02 molar equivalents wrt. Compound 15) then tert-butyl dimethylsilyl chloride (4.99 molar equivalents wrt compound 15) were added. The reaction was stirred at RT for 2 hours. Ice water was added and the reaction stirred for 20 minutes. The organic layer was separated, the aqueous layer extracted two times with ethyl acetate, the combined organic fractions were washed with dilute brine, dried over anhydrous MgSO4, filtered, and condensed under vacuum to yield brown oil. The oil was purified by column chromatography using silica gel and 97:3 heptanes:ethyl acetate then 95:5 heptanes: ethyl acetate as the eluant.

Compound 17: NaH (1.1 molar equivalents wrt compound 1) was stirred, under $N_2$, in an ice bath and toluene was added. Triethyl phosphonoacetate (1.01 molar equivalents wrt compound 16) was slowly added so that the temperature did not exceed 10° C. The reaction was stirred on ice until all observed effervescence stopped. The reaction was removed from the ice bath and compound 16 (bis-OTBS acetone) was added drop-wise. The reaction was stirred at RT for 1.5 hours and ethanol was added to dissolve a precipitate that had formed. Water was added to quench the reaction. The organic layer was separated, the aqueous layer extracted once with ethyl acetate, and the combined organic layers were washed with brine and dried over anhydrous $MgSO_4$. The organic solution was filtered and condensed under vacuum to yield yellow oil. The oil was purified by column chromatography using silica gel and 98:2 heptanes: ethyl acetate.

Compound 18: Compound 2 was stirred in ether and cooled, under $N_2$, to –80° C. in an acetone/dry ice bath. Diisobutyl aluminum hydride (1.5 molar equivalents wrt compound 17) was added drop wise. The reaction was removed from the acetone/dry ice bath, warmed to RT, and stirred at RT for 50 minutes. The reaction was cooled in an acetone/dry ice bath and water was added drop wise to quench the reaction. The acetone/dry ice bath was removed and 20% NaOH (molar equivalents wrt compound 17), dichloromethane, and Rochelle salt (KNa tartrate tetrahydrate) were added. The organic layer was separated, the aqueous layer extracted two times with dichloromethane, and the organic fractions were combined, washed with water and dried first with $K_2CO_3$ and then $MgSO_4$. The dried organics were filtered and condensed under vacuum to yield clear oil. The clear oil was purified by column chromatography using silica gel and 9:1 heptanes:ethyl acetate as the initial eluant then changing to 8:2 heptanes:ethyl acetate.

Compound 19: Compound 18 was stirred in dichloromethane, under $N_2$, and cooled to below 0° C. in an acetone/ice bath. Triethylamine (1.2 molar equivalents wrt compound 18) was added and the reaction cooled to below 0° C. Methane sulfonyl chloride (1.3 molar equivalents wrt compound 18) was added slowly while monitoring the temperature to assure that it did not exceed 5° C. The reaction stirred cold for 1 hour then dichloromethane and water were added. The organic layer was separated, the aqueous layer extracted with dichloromethane, the combined organic layers were dried with $K_2CO_3$ and $MgSO_4$, filtered and condensed under vacuum to yield the mesylate intermediate. The product was used without further purification.

Compound 20: NaH (1.25 molar equivalents wrt compound 18) was stirred with dimethyl formamide, under $N_2$, and a polyamine side chain (1.15 molar equivalents wrt compound 18), of chosen length, dissolved in tetrahydrofuran was slowly added. The reaction stirred at RT until the evolution of $H_2$ gas ceased. Starting material mesylate was slowly added (compound 4, step 1 product) and stirred at RT for several hours. Upon completion, as evidenced by TLC, the reaction contents were condensed under vacuum. The crude semisolid was dissolved in ethyl acetate and water. The organic layer was separated; the aqueous layer extracted twice with ethyl acetate, the combined organic layers were washed with water and condensed under vacuum. The product was purified by column chromatography using silica gel and 75:25 heptanes:ethyl acetate as the eluant.

Compound 21: Compound 20 was stirred in methanol at RT. Concentrated HCl (2 molar equivalents wrt compound 20) was slowly added. The reaction stirred at RT for 30 minutes or until reaction was complete as evidenced by TLC with 60:40 heptanes:ethyl acetate as the mobile phase. The reaction contents were condensed under vacuum and purified by column chromatography using silica gel and 95:5 dichloromethane: methanol as the eluant.

Compound 22: Compound 21 diol was stirred in dichloromethane, under $N_2$, in an ice/MeOH bath. Benzoyl Chloride (1.03 molar equivalents wrt compound 21) was added. Once the reaction reached <10° C., pyridine (1.04 molar equivalents wrt compound 21) was slowly added. The reaction was stirred in the ice/methanol bath for 1 hour and completeness was determined by TLC using 1:1 heptanes:ethyl acetate as the mobile phase. Once reaction was complete, water was added and the reaction stirred for 15 minutes in the ice/methanol bath. The organic layer was separated; the aqueous layer extracted with dichloromethane, the combined organic layers were washed once with water, dried over anhydrous $MgSO_4$, filtered and condensed under vacuum. The product was purified by column chromatography using silica gel and 7:3 heptanes:ethyl acetate as the eluant.

Compound 23: Compound 22 was stirred in toluene, under $N_2$, at <5° C. Phosphorus tribromide (1.1 molar equivalents wrt compound 22) was slowly added. The reaction was removed from the ice bath and stirred at RT for 30 minutes or until the reaction was complete as determined by TLC using 95:5 dichloromethane: methanol as the mobile phase. Upon completion the reaction was returned to the ice bath, water was slowly added, and the reaction was stirred for 15 minutes. The organic layer was separated, the aqueous layer extracted two times with ethyl acetate, the combined organic layers were washed with 2% (w:v) NaHCO3 and then brine, dried over $K_2CO_3$ and $MgSO_4$, filtered and condensed under vacuum. The product was used without further purification.

Compound 24: NaH (1.2 molar equivalents wrt compound 23) was stirred in dimethyl formamide, under $N_2$, at RT and a polyamine side chain (1.2 molar equivalents wrt compound 23), of chosen length, dissolved in tetrahydrofuran was added slowly. The reaction stirred at RT until the evolution of $H_2$ gas ceased. Compound 23, dissolved in tetrahydrofuran, was slowly added and the reaction was stirred at RT for several hours. Reaction completeness was determined by TLC using 80:20 toluene:ethyl acetate as the mobile phase. The reaction was condensed under vacuum; the crude was dissolved in ethyl acetate and water. The organic layer was separated, the aqueous layer was extracted with ethyl acetate, and the combined organic layers were washed with brine, and condensed under vacuum. The product was used without further purification.

Compound 25: Compound 24 was stirred in tetrahydrofuran, under $N_2$, at RT. Methanol then sodium methoxide (1.5 molar equivalents wrt compound 24) were added and the reaction was stirred at RT for 30 minutes. Reaction completeness was determined by TLC using 80:20 toluene:ethyl acetate as the mobile phase. Concentrated HCl (molar equivalents wrt sodium methoxide) was added to neutralize the sodium methoxide and the reaction contents were condensed under vacuum. Ethyl acetate and water were added to the crude product. The organic layer was separated, the aqueous layer washed once with ethyl acetate and once with dichloromethane, the combined organic layers dried with $NaSO_4$, filtered and condensed under vacuum. The product was purified by column chromatography using silica gel and 8:2 toluene: ethyl acetate as the eluant.

Scheme 3:

Compound 28: Compound 26 was stirred in dichloromethane, under $N_2$, at −10° C. in an ice/methanol bath. Triethylamine (2 molar equivalents wrt to compound 26) was added and the reaction was again cooled to −10° C. Methane sulfonyl chloride (2.5 molar equivalents wrt compound 26) dissolved in methylene chloride was added slowly and the reaction stirred cold for 1 hour. Reaction completeness is monitored by TLC using 8:2 heptanes: ethyl acetate. Water was slowly added to quench the reaction. The organic layer was separated, the water layer extracted with dichloromethane, the combined organic layers were washed with brine and condensed under vacuum. The reactive intermediate was used immediately without further purification.

Compound 29: Potassium thioacetate (2.5 molar equivalents wrt compound 26) in dimethylformamide was stirred, under $N_2$, at RT. Compound 28 mesylate in dimethylformamide was slowly added and the reaction was stirred overnight. The reaction was condensed under vacuum and the solids dissolved in ethyl acetate and water. The organic layer was separated, the aqueous layer back extracted with ethyl acetate, the combined organic layers were washed with brine and condensed under vacuum. The product was purified by column chromatography using silica gel and 8:2 toluene: ethyl acetate as the eluant.

Compound 31: NaH (1.25 molar equivalents wrt compound 26) was stirred, under $N_2$, at RT and dimethylformamide was added. Mesitylene methyl sulfonamide dissolved in tetrahydrofuran was slowly added and the reaction was stirred until the evolution of $H_2$ gas ceased. Compound 28 mesylate dissolved in tetrahydrofuran was slowly added and the reaction was stirred overnight. The reaction was condensed under vacuum and the solids dissolved in ethyl acetate and water. The organic layer was separated, the aqueous layer extracted with ethyl acetate, the combined organic layers were washed with brine and condensed under vacuum. The product was purified by column chromatography using silica gel and 8:2 toluene:ethyl acetate as the eluant.

Compound 33: NaH (1.25 molar equivalents wrt compound 26) was stirred, under $N_2$, at RT and dimethylformamide was added. Mesitylene dimethyl sulfonamide dissolved in tetrahydrofuran was slowly added and the reaction stirred until the evolution of $H_2$ gas ceased. Compound 28 mesylate dissolved in tetrahydrofuran was slowly added and the reaction was stirred overnight. The reaction was condensed under vacuum and the solids dissolved in ethyl acetate and water. The organic layer was separated, the aqueous layer extracted with ethyl acetate, the combined organic layers were washed with brine and condensed under vacuum. The product was purified by column chromatography using silica gel and 8:2 toluene:ethyl acetate as the eluant.

Compound 35: NaH (1.25 molar equivalents wrt compound 26) was stirred, under $N_2$, at RT and dimethylformamide was added. Mesitylene ethyl sulfonamide dissolved in tetrahydrofuran was slowly added and the reaction stirred until the evolution of H2 gas ceased. Compound 28 mesylate dissolved in tetrahydrofuran was slowly added and the reaction stirred overnight. The reaction was condensed under vacuum and the solids dissolved in ethyl acetate and water. The organic layer was separated, the aqueous layer extracted with ethyl acetate, the combined organic layers were washed with brine and condensed under vacuum. The product was purified by column chromatography using silica gel and 8:2 toluene:ethyl acetate as the eluant.

Removal of Mesitylene Protective Groups:

Compounds 30, 32, 34, and 36: Starting material was stirred in dichloromethane at RT and phenol (11 molar equivalents per mesitylene group) was added. 30% HBr in acetic acid was slowly added (13 molar equivalents per mesitylene group) and the reaction was tightly sealed and stirred for 24-72 hours at RT. Water was added and the reaction stirred for 30 minutes at RT. The organic layer was separated, the aqueous layer was washed five times with dichloromethane, and the water layer was condensed under vacuum. 30% NaOH was added to the oil and stirred for several minutes to make the free base. Dichloromethane was added and stirred for several more minutes. The organic layer was separated, the water layer was extracted five times with dichloromethane, and the combined organic layers were condensed under vacuum. The HCl salt was made by stirring the free base in ethanol and slowly adding concentrated HCl (4 molar equivalents per free amine). The reaction was condensed under vacuum and the solids were recrystallized in a hot ethanol/water mixture.

EXAMPLE 2

Biological Assay for Efficacy in Preventing Alopecia

The efficacy of chemotherapeutic polyamines in reducing or preventing chemotherapy-induced alopecia in a rat model was examined. This animal model mimics many of the features found in chemotherapy-induced alopecia seen in humans and is considered a clinically relevant model for testing novel therapeutics.

Induction of alopecia by cytoxan (CTX). Lactating Sprague Dawley mother rats with rat pups were purchased from Harlan Sprague Dawley (Indianapolis, Ind.). The mother rats were given food and water ad libitum. The rats pups were tested in the model of chemotherapy-induced alopecia described by Hussein A. M. et al., Science: 249, 1564 (1990). Cytoxan (CTX), a chemotherapeutic widely used in the treatment of cancer, was used to induce alopecia in the rats. A common side effect of cytoxan in patients is alopecia. Cytoxan was purchased from Sigma Chemicals Co. (St. Louis, Mo.). To produce CTX-induced alopecia, 7 to 10 day old rat pups were injected i.p. with 35 mg/kg of CTX prepared in phosphate-buffered saline. It was observed that 35 ug/gm of CTX was sufficient to induce 100% hair loss approximately 7 days after cytoxan challenge.

Chemoprotective polyamines of the invention were prepared in a delivery vehicle consisting of from 60-100% ethanol in water, depending on the solubility of the compound. The compounds in ethanol/water solution from 50-150 µl in volume were topically administered to the backs of the pups once per day before and after CTX challenge. Using a micropipette, the formulation was applied to approximately 2 cm² section of skin to the backs of the rat pups. Specifically, the pups were treated once daily for the 4-5 days before CTX challenge, once on the day of CTX challenge and once daily for 5 days afterwards. Control groups consisted of pups receiving only delivery vehicle. Control groups treated with delivery vehicle were tested as part of every treatment study. Two or more animals were tested per group in both the control and test groups.

Approximately 7 to 10 days after CTX treatment, the pups were evaluated for alopecia. Hair loss was evaluated using a modified alopecia-scoring index described by Chen G. et al., Int. J. Cancer: 75, 303 (1998). A score of 0=no hair loss; a score of 1=10-30% hair loss; a score of 2=40-60% hair loss; a score of 3=70-90% hair loss; and a score of 4=100% hair loss.

EXAMPLE 3

Biological Assay for Efficacy in Preventing Dermatitis

To determine efficacy of chemoprotective polyamines in preventing radiation-induced dermatitis, adult rats were topically treated with the compounds before and after radiation treatment. Rats were exposed to medically relevant levels of radiation that could induce clinical radiation dermatitis. Sprague Dawley rats (Harlen Spraque Dawley) at 4-6 weeks-old were anesthetized with sodium pentobarbital at 40 mg/kg body weight (Sigma, St. Louis, Mo.) prior to radiation exposure. A defined, depilated area on the backs of rats was irradiated using a Mark I, Model 30, Cs 137 irradiator (J. L. Sheppard & Associates). Briefly, the back was stripped of hair to expose the skin using a 1:1 rosin/beeswax mixture. The rest of the body was protected from radiation exposure using a lead shield. A dose response study was initially preformed to reproduce relevant dermatitis that matched the Grade (I-IV) scale used to score the severity of radiation-induced dermatitis in the clinical setting. Radiation doses of 5-7 Gray (1 Gray (Gy)=100 mrem) produced Grade I dermatitis within 8-10 days. Radiation doses of 7-10 Gy produced Grade II dermatitis within 8-10 days. After 8-10 days, severe radiation dermatitis was produced at 20-25 Gy (Grade III dermatitis) or at 30-35 Gy (Grade IV). Radiation dermatitis of Grade II-III was considered most clinically relevant, so a radiation challenge dose of 15 Gy in the rats was used. The stripped back region on the rats was treated topically with chemoprotective polyamine once daily for 5 days before and 5 days after radiation challenge.

The polyamines were prepared in a delivery vehicle, consisting of from 60-100% ethanol in water, depending on the solubility of the compound. The compounds in ethanol/water solution from 100-150 µl in volume were topically administered to the stripped region. Rats treated with only the delivery vehicle served as controls. Eight to ten days post-radiation challenge, the rats were evaluated for dermatitis using a modified scoring scale described by Masuda K. et al. Int. J. Radiation Oncol. Biol. Phys: 12, 1645 (1986). Dermatitis score of 0=normal, 1=slight redness, scaly skin with no focal lesions, 2=moderate redness, breakdown of larger area, some small focal lesions, 3=skin very red, breakdown of most of the irradiated area, large ulcers and crusty lesions, 4=skin very red, breakdown of the entire irradiated area, severe exudation and large crusty lesions.

EXAMPLE 4

Radiation-induced Mucositis Model in Hamsters

The model for radiation-induced oral mucositis was developed for the purpose of screening and identifying effective polyamines useful for treatment. The model used in this example was derived from the oral mucositis model described by Sonis S. T. et al. (Oral Oncology 36:373-381, 2000). Male golden Syrian hamsters (70-95 gram, 35-42 days, Charles River Laboratories, Wilmington, Mass.) were used. Animals were individually numbered, housed in small groups and fed and watered ad libitum. Hamsters were anesthetized with sodium pentobarbital (80 mg/kg body weight, Sigma, St. Louis, Mo.). The left buccal cheek pouch was everted and secured. A protective lead shield covered the remainder of the animal. Subsequently, the cheek pouch was irradiated with a single dose of radiation from 10 to 50 Gy delivered to the targeted mucosa in the 137 Cs Irradiator. Starting 10 to 12 days after radiation, the severity of mucositis was assessed every two days. The severity level of mucositis was evaluated using a modified mucositis scoring system described by Sonis S. T. et al. (Oral Oncology 36:373-381, 2000) The scoring system was as follows:

0=Pouch completely healthy. No erythema or vasodilatation.
1=Erythema.
2=Severe erythema, vasodilatation
3=Severe erythema and vasodilatation. Superficial erosion on radiated pouch surface area.
4=Formation of ulcers in one or more places. Cumulative ulcer formation about up to 50% of radiated pouch surface area. Diminished pliability of mucosa
5=Virtually more then 50% or complete ulceration of the radiated pouch mucosa. Loss of pliability.

Manifestations of radiation-induced mucositis were observed by day 12. The hamster buccal pouches were evaluated for the presence of mucositis and photographed every two days from day 12 to day 20. Mucositis was found to increase in severity, reaching a peak at day 16. An obvious dose response of radiation was seen, and the grades of mucositis at day 16 were scored as:

| Treatment | Mucositis Grade* |
| --- | --- |
| 0 Gy | 0 |
| 10 Gy | 1 |
| 20 Gy | 2 |
| 30 Gy | 2.5 |
| 40 Gy | 4 |
| 50 Gy | 5 |

*0 = Pouch completely healthy - no erythema or vasodilatation. 1 = Erythema. 2 = Severe erythema, vasodilatation. 3 = Severe erythema and vasodilatation; superficial erosion on radiated pouch surface area. 4 = Formation of ulcers in one or more places; culmulative ulcer formation about up to 50% of radiated pouch surface area; diminished pliability of mucosa. 5 = Virtually more than 50% or complete ulceration of the radiated pouch mucosa; loss of pliability.

The present invention is not limited to the embodiments described and exemplified above, but is capable of variation and modification within the scope of the appended claims.

What is claimed:
1. A compound of Formula I:

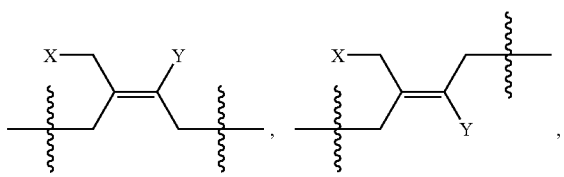

wherein:
each Z is independently a member selected from the group consisting of:

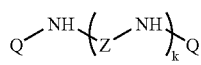

-continued

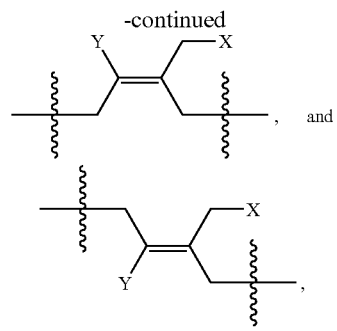

X is a member selected from the group consisting of D and —$R^2$-D;
Y is a member selected from the group consisting of H, alkyl, and $R^3$-D;
D is a member selected from the group consisting of —OH, —SH, —$SR^4$, and —$N^4R^5$;
each $R^2$, $R^3$, $R^6$, and $R^7$ is independently $C_{1-6}$ alkylene;
$R^4$ is a member selected from the group consisting of H and lower alkyl;
$R^5$ is a member selected from the group consisting of H, lower alkyl, and —$R^6$-D;
Q is a member selected from the group consisting of H, lower alkyl, and —$R^7$—$SR^4$; and
k is an integer from 2 to about 16;
stereoisomers, prodrugs, pharmaceutically acceptable salts, monoprotonated acid salts, or polyprotonated acid salts thereof.

2. A compound of claim 1, wherein Y is a member selected from the group consisting of H and $R^3$-D.
3. A compound of claim 2, wherein Y is H.
4. A compound of claim 2, wherein Y is $R^3$-D.
5. A compound of claim 3, wherein X is D.
6. A compound of claim 3, wherein X is $R^2$-D.
7. A compound of claim 4, wherein X is D.
8. A compound of claim 4, wherein X is $R^2$-D.
9. A compound of claim 1, wherein k is an integer from 2 to 8.
10. A compound of claim 1, wherein k is an integer from 9 to about 16.
11. A compound of claim 1, wherein k is an integer from 9 to 12.
12. A compound of claim 1, wherein k is 2.
13. A compound of claim 1, wherein k is 3.
14. A compound of claim 1, wherein k is 4.
15. A compound of claim 1, wherein k is 5.
16. A compound of claim 1, wherein k is 6.
17. A compound of claim 1, wherein k is 7.
18. A compound of claim 1, wherein k is 8.
19. A compound of claim 2 wherein Q is a member selected from the group consisting of H and lower alkyl.
20. A pharmaceutical preparation comprising:
at least one compound of Formula I of claim 1, and
a topical delivery vehicle for locally delivering the compound to dermal or mucosal cell members selected from the group consisting of skin, scalp, mouth, nasoesophageal, gastrointestinal and urogenital system.
21. The pharmaceutical preparation of claim 20, further comprising at least one other agent that reduces hair loss, dermatitis, mucositis or gastrointestinal distress caused by treatment with a chemotherapeutic agent or radiation therapy.
22. The pharmaceutical preparation of claim 21, wherein the other agent is an anti-proliferative agent.

23. The pharmaceutical preparation of claim 21, wherein the other agent is a chemoprotective inducing agent.

24. The pharmaceutical preparation of claim 21, wherein the other agent is a free radical scavenger.

25. The pharmaceutical preparation of claim 20, wherein the topical delivery vehicle comprises one or more members selected from the group consisting of liposomes, lipid droplet emulsions, oils, aqueous emulsions of polyoxyethylene ethers, aqueous alcohol mixtures, aqueous ethanol mixtures containing propylene glycol, aqueous ethanol mixtures containing phosphatidyl choline, lysophosphatidyl choline and triglycerides, xanthan gum in aqueous buffer, hydroxypropylmethylcellulose in aqueous buffer or aqueous alcohol mixtures, diethylene glycol monoethyl ether in aqueous buffer, and biodegradable microparticles.

26. The pharmaceutical preparation of claim 25, wherein the delivery vehicle comprises an aqueous alcohol mixture.

27. The pharmaceutical preparation of claim 26, wherein the delivery vehicle further comprises propylene glycol.

28. The pharmaceutical preparation of claim 27, in the form of a cream, lotion, ointment or gel.

29. The pharmaceutical preparation of claim 25, wherein the delivery vehicle comprises a mucoadhesive substance.

30. The pharmaceutical preparation of claim 29, in the form of an aerosol, oral rinse, ointment or gel.

31. The pharmaceutical preparation of claim 25, in the form of a cream, ointment, lotion, gel, foam or suppository.

32. The pharmaceutical preparation of claim 25, wherein the delivery vehicle comprises one or more members selected from the group consisting of nonionic liposomes and mucoadhesive substances.

33. The pharmaceutical preparation of claim 32, in the form of a liquid for coating the surface of the gastrointestinal tract.

34. A method for reducing hair loss dermatitis, mucositis or gastrointestinal distress in a patient undergoing treatment with a chemotherapeutic agent or radiation therapy, comprising:
   administering to the patient a therapeutically effective amount of a pharmaceutical preparation comprising at least one compound of Formula I of claim 1, and
   a topical delivery vehicle for locally delivering the compound to dermal or mucosal cell members selected from the group consisting of skin, scalp, mouth, nasoesophageal, gastrointestinal and urogenital system.

35. The method of claim 34, comprising administering the pharmaceutical preparation beginning at least one day prior to chemotherapy or radiation therapy.

36. The method of claim 35, comprising administering the pharmaceutical preparation beginning at least five days prior to chemotherapy or radiation therapy.

37. The method of claim 34, comprising administering the pharmaceutical preparation after initiation of chemotherapy or radiation therapy.

38. The method of claim 34, comprising administering the pharmaceutical preparation throughout a course of chemotherapy or radiation therapy.

39. The method of claim 34, comprising administering the pharmaceutical preparation following termination of a course of chemotherapy or radiation therapy.

40. The method of claim 34, further comprising administering to the patient at least one other agent that reduces hair loss, dermatitis, mucositis or gastrointestinal distress caused by treatment with a chemotherapeutic agent or radiation therapy.

41. A method of treating cancer to increase a patient's tolerance to high doses of a chemotherapeutic agent or radiation therapy, the method comprising:
   administering one or more pharmaceutical preparations, in an amount and for a time to reduce one or more members selected from the group consisting of chemotherapy—or radiation therapy-induced hair loss, dermatitis, mucositis and gastrointestinal distress, thereby increasing the patient's tolerance to the high dose of the chemotherapeutic agent or radiation therapy, the pharmaceutical preparation comprising:
   a compound of Formula I of claim 1, and
   a topical delivery vehicle for locally delivering the compound to dermal or mucosal cell members selected from the group consisting of skin, scalp, mouth, nasoesophageal, gastrointestinal and urogenital system.

42. A compound according to the structure

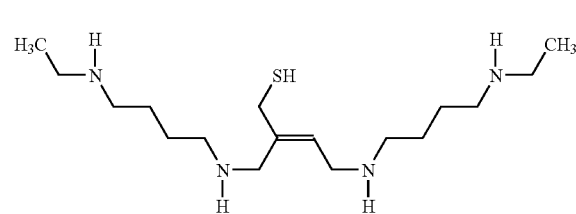

stereoisomers, prodrugs, pharmaceutically acceptable salts, monoprotonated acid salts, or polyprotonated acid salts thereof.

* * * * *